US007785580B2

(12) United States Patent
Pan et al.

(10) Patent No.: US 7,785,580 B2
(45) Date of Patent: Aug. 31, 2010

(54) MODIFIED IL-4 MUTEIN RECEPTOR ANTAGONISTS

(75) Inventors: Clark Pan, Sudbury, MA (US); Steve Roczniak, Madison, AL (US); Jeffrey Michael Greve, Berkeley, CA (US); Stephanie L. Yung, San Francisco, CA (US); Malinda Longphre, Oakland, CA (US); Teresa Mo-Fun Wong, Lafayette, CA (US); Adrian Tomkinson, El Cerrito, CA (US); David Boisvert, El Cerritto, CA (US); Elise Burmeister-Getz, Berkeley, CA (US); Kathy Delaria, Walnut Creek, CA (US)

(73) Assignee: Aerovance, Inc., San Diego, CA (US)

( * ) Notice: Subject to any disclaimer, the term of this patent is extended or adjusted under 35 U.S.C. 154(b) by 0 days.

(21) Appl. No.: 11/940,217

(22) Filed: Nov. 14, 2007

(65) Prior Publication Data

US 2009/0010874 A1 Jan. 8, 2009

Related U.S. Application Data

(63) Continuation-in-part of application No. 10/820,559, filed on Apr. 8, 2004, now Pat. No. 7,404,957.

(60) Provisional application No. 60/498,906, filed on Aug. 29, 2003, provisional application No. 60/528,228, filed on Dec. 9, 2003, provisional application No. 60/530,182, filed on Dec. 17, 2003.

(51) Int. Cl.
*A61K 38/20* (2006.01)
*A61K 38/00* (2006.01)
*C07K 14/47* (2006.01)
*C12P 21/06* (2006.01)

(52) U.S. Cl. ...................... 424/85.2; 435/69.5; 514/12; 530/351

(58) Field of Classification Search ...................... None
See application file for complete search history.

(56) References Cited

U.S. PATENT DOCUMENTS

| | | | | |
|---|---|---|---|---|
| 5,206,344 | A * | 4/1993 | Katre et al. | 530/351 |
| 5,783,181 | A | 7/1998 | Browne et al. | |
| 5,986,059 | A | 11/1999 | Shanafelt et al. | |
| 6,028,176 | A | 2/2000 | Greve et al. | |
| 6,130,318 | A | 10/2000 | Wild et al. | |
| 6,608,183 | B1 | 8/2003 | Cox, III | |
| 2003/0194745 | A1 * | 10/2003 | McDowell et al. | 435/7.1 |
| 2005/0059590 | A1 | 3/2005 | Pan et al. | |
| 2007/0048219 | A1 | 3/2007 | Hsei et al. | |

FOREIGN PATENT DOCUMENTS

| | | | |
|---|---|---|---|
| WO | WO 98/03654 | A2 | 1/1998 |
| WO | WO 98/03654 | A3 | 1/1998 |

OTHER PUBLICATIONS

Gee et al., "Differential Effect of IL-4 and IL-13 on CD44 Expression in the Burkitt's Lymphoma B Cell Line BL30/B95-8 and in Epstein-Barr Virus (EBV) Transformed Human B Cells:. Loss of IL-13 Receptors on Burkitt's Lymphoma B Cells", *Cell. Immunol.*, 211:131-142 (2001).

Henderson et al., "Soluble IL-4 Receptor Inhibits Airway Inflammation Following Allergen Challenge in a Mouse Model of Asthma", *J. Immunol.*, 164(2):1086-1095 (2000).

Huang et al., "IL-13 Expression at the Sites of Allergen Challenge in Patients with Asthma," *J. Immunol.*, 155(5):2688-2694 (1995).

Kips et al., "New anti-asthma therapies: suppression of the effect of interleukin (IL)-4 and IL-5", *European Respiratory Journal*, 17:499-506 (2001).

Kreitman et al., "Site-Specific Conjugation to Interleukin 4 Containing Mutated Cysteine Residues Produces Interleukin 4-Toxin Conjugates with Improved Binding and Activity", *Biochemistry*, 33:11637-11644 (1994).

Kruse et al., "Conversion of human interleukin-4 into a high affinity antagonist by a single amino acid replacement", *The EMBO Journal.*, 11 (9):3237-3244 (1992).

Kryworuchko et al., "Regulation of CD44-Hyaluronan Interactions in Burkitt's Lymphoma and Epstein-Barr Virus-Transformed Lymphoblastoid B Cells by PMA and Interleukin-4", *Cell. Immunol.*, 194:54-66 (1999).

Levens et al., "Micro-environmental factors in the survival of human B-lymphoma cells", *Cell Death & Differ.*, 7:59-69 (2000).

Myers et al., "Growth Stimulation of Human Head and Neck Squamous Cell Carcinoma Cell Lines by Interleukin 4", *Clin. Cancer Res.*, 2:127-135 (1996).

Newcom et al., "Interleukin-4 Is an Autocrine Growth Factor Secreted by the L-428 Reed-Sternberg Cell", *Blood*, 79(1):191-197 (1992).

Tony et al., "Design of human interteukin-4 antagonists inhibiting interleukin-4-dependent and interleukin-13-dependent responses in T-cells and B-cells with high efficiency", *Eur. J. Biochem.*, 225:659-665 (1994).

Ying et al., "Expression of IL-4 and IL-5 mRNA and Protein Product by CD4+ and CD8+ T Cells, Eosinophils, and Mast Cells in Bronchial Biopsies Obtained from Atopic and Nonatopic (Intrinsic) Asthmatics", *The Journal of Immunology*, 158(7):3539-3544 (1997).

Zhu et al. "Pulmonary expression of interleukin-13 causes inflammation, mucus hypersecretion, subepithelial fibrosis, physiologic abnormalities, and eotaxin production", *J. Clin. Invest.*, 103(6):779-788 (1999).

* cited by examiner

*Primary Examiner*—Bridget E Bunner
*Assistant Examiner*—Fozia M Hamud
(74) *Attorney, Agent, or Firm*—DLA Piper LLP (US)

(57) ABSTRACT

This invention relates to modified IL-4 mutein receptor antagonists comprising an IL-4 mutein receptor antagonist coupled to polyethylene glycol. Related formulations and dosages and methods of administration thereof for therapeutic purposes are also provided. These modified IL-4 mutein receptor antagonists, compositions and methods provide a treatment option for those individuals afflicted with a respiratory disorder such as asthma by inhibiting IL-4 and IL-13-mediated airway hyperresponsiveness and eosinophilia. More particularly, these antagonists have an increased duration of effect versus unmodified IL-4RA by virtue of a greater plasma half-life.

17 Claims, 2 Drawing Sheets mPEG-MAL 22 kD
Linear PEG

Chemistry of PEGylation reaction

95% confidence intervals

| | EC50 |
|---|---|
| IL-4DM | 0.1116 to 0.1605 |
| IL-4TM 40Branch | 0.1209 to 0.1639 |
| IL-4DM 40Branch | 1.132 to 1.740 |

MODIFIED IL-4 MUTEIN RECEPTOR ANTAGONISTS

CROSS REFERENCE TO RELATED APPLICATION(S)

This application is a continuation-in-part of U.S. Ser. No. 10/820,559, filed Apr. 8, 2004, which claims the benefit of priority under 35 U.S.C. §119(e) of U.S. Ser. No. 60/498,906, filed Aug. 29, 2003, of U.S. Ser. No. 60/528,228, filed Dec. 9, 2003, and of U.S. Ser. No. 60/530,182, filed Dec. 17, 2003, the entire contents of which are incorporated herein by reference.

BACKGROUND OF THE INVENTION

1. Field of the Invention

This invention relates to an IL-4 mutein receptor antagonist coupled to a non-protein polymer such as polyethylene glycol. In addition, related formulations, dosages 15 and methods of administration thereof for therapeutic purposes are provided. These modified IL-4 mutein receptor antagonists, and associated compositions and methods are useful in providing a treatment option for individuals afflicted with severe asthma, chronic obstructive pulmonary disease, and related lung conditions.

2. Background Information

Asthma is characterized by variable, reversible airflow obstruction, and airway hyperresponsiveness (AHR), associated with an infiltration of the bronchial mucosa with activated T-lymphocytes (T-cells), and eosinophils. These cells, along with resident airway mast cells, secrete a variety of cytokines and mediators that play a fundamental role in the pathogenesis of the disease. CD4+ Th2 cells, through the release of specific cytokines (IL-4, IL-5, IL-9, and IL-13), are thought to orchestrate the disease process (1,2). In particular, the Th2 cytokines IL-4, and IL-13, are considered pivotal to the development and maintenance of airway inflammation and airway hyperresponsiveness.

A number of in vivo studies also support the pivotal role of IL-4 and IL-13 in the pathogenesis of asthma. Using animals deficient in either cytokine, or reagents that neutralize either IL-4 or IL-13 function, an important role of these cytokines is observed in regulating the primary and secondary immune response leading to airway inflammation and airway hyperresponsiveness (3, 4). Cumulatively, these data suggest that IL-4 and IL-13 may play both overlapping and independent roles in the allergic airways response, and that targeting both cytokines could have significant added benefit to targeting either cytokine alone.

Antagonists of IL-4 have been reported in the literature. Mutants of IL-4 that function as antagonists include the IL-4 antagonist mutein IL-4/Y124D (Kruse, N., et al., Conversion of human interleukin-4 into a high affinity antagonist by a single amino acid replacement, *Embo J.* 11:3237-44, 1992) and a double mutein IL-4-[R121D/Y124D] (Tony, H., et al., Design of Human Interleukin-4 Antagonists in Inhibiting Interleukin-4-dependent and Interleukin-13-dependent responses in T-cells and B-cells with high efficiency, *Eur. J. Biochem.* 225:659-664 (1994)). The single mutein is a substitution of tyrosine by aspartic acid at position 124 in the D-helix. The double mutein is a substitution of Arginine by Aspartic Acid at position 121, and of tyrosine by aspartic acid at position 124 in the D-helix. Variations in this section of the D helix positively correlate with changes in interactions at the second binding region.

Mutant variants of IL-4 demonstrating agonism or antagonism of wild-type IL-4 may be useful for treating conditions associated with one of the pleiotropic effects of IL-4. For instance, antagonists of IL-4 would be useful in treating conditions exacerbated by IL-4 production such as asthma, allergy, or other inflammatory response-related conditions. Agonists of IL-4 may be useful for treating conditions wherein the presence of IL-4 is associated with the amelioration or attenuation of a disease, for example, an autoimmune disease such as Rheumatoid Arthritis, Multiple Sclerosis, Insulin-dependent Diabetes Mellitus, etc. These autoimmune diseases are characterized by a polarization in production of the T helper cell populations, types 1 and 2 (Th1, Th2). Naive CD4+ T cells differentiate into Th1 or Th2 subsets, depending on the cytokine present during stimulation. An IL-4 agonist would ideally shift production to the T-helper cell desired, i.e., towards Th2, thereby having a therapeutic effect.

PCT/US93/03613 discloses an IL-4 variant having a Phe-Leu or Tyr-Leu sequence in a alpha-helical domain and a negatively-charged amino acid within two amino acids immediately upstream or downstream from the Phe-Leu or Tyr-Leu sequence, the variant having an increased affinity for the IL-4 receptor by virtue of a neutral amino acid substituted for the negatively-charged amino acid. It also discloses that the specific substitution of Trp-Leu or Phe-Leu within an a-helix of IL-4 within 2-residues of a negatively charged residue results in improved affinity. The variant is an IL-4 fusion protein (with diphtheria toxin).

A recombinant mutein protein (IL-4RA) derived from human IL-4 mutated in two positions of its amino acid sequence was previously reported in U.S. Pat. Nos. 6,028,176 and 6,313,272. IL-4RA binds with high affinity to the human IL-4 receptor alpha chain, an important functional signaling component of both the IL-4 and IL-13 receptor complexes. This mutein has no agonist activity, and acts as a potent competitive IL-4 and IL-13 receptor antagonist in vitro (See U.S. Pat. Nos. 6,028,176 and 6,313,272). A significant drawback to the use of IL-4RA is its relatively short half life in vivo (approximately 3-6 hrs). Pharmacokinetic/pharmacodynamic modeling of IL-4RA in the primate asthma model indicates that the effective average steady state concentration for optimal therapeutic effect is approximately 60 ng/ml.

One approach to overcoming the short half life is frequent administration of the IL-4RA mutein to a patient, however frequent administration (usually by injection or tracheal intubation) creates very significant barriers to patient acceptance of the therapy and therapeutic administration in a clinic.

SUMMARY OF THE INVENTION

The invention provides IL-4RA muteins with greater half life than previously reported muteins. The invention also provides reagents and methods of inhibiting IL-4 and IL-13-mediated immune responses. This and other aspects of the invention are provided by one or more of the embodiments listed below.

In one embodiment, the invention provides a purified preparation of a modified IL-4 mutein receptor antagonist comprising an IL-4 mutein receptor antagonist coupled to a non-protein polymer selected from the group consisting of polyethylene glycol, polypropylene glycol and polyoxyalkylenes. In one aspect of this embodiment, the purified preparation comprises a modified IL-4 mutein receptor antagonist polypeptide comprising the amino acid sequence as set forth in SEQ ID NO: 32. In one aspect of this embodiment, the purified preparation comprises a modified IL-4 mutein receptor antagonist polypeptide comprising the amino acid sequence as set forth in SEQ ID NO: 33. In another aspect of this embodiment, the polyethylene glycol (PEG) is linear or branched, and has a molecular weight ranging from about 3 kD to 50 kD. In one embodiment, the PEG moiety is about 40 kD.

In one embodiment, the modified IL-4 mutein receptor antagonist polypeptide can be coupled to a non-protein polymer at amino acid residue at position 28, 36, 37, 38, 104, 105 or 106 of IL-4. Such positions are numbered according to the wild type IL-4 (i.e. human interleukin-4) amino acid sequence. In one aspect of this embodiment, the amino acid residue at positions 28, 36, 37, 38, 104, 105 or 106 is cysteine. In another aspect of this embodiment, the amino acid residue at positions 121, 124 and 125 is aspartic acid.

In one embodiment, a modified mutein receptor antagonist of the invention binds to the IL-4 receptor alpha chain with a $K_D$ of about 0.1 nM to about 10 μM, about 0.5 nM to about 1 μM, or about 1.0 nM to about 100 nM.

In another embodiment, the modified IL-4 mutein receptor antagonist inhibits the proliferative response of TF-1 cells to IL-4 with an $IC_{50}$ of about 0.1 nM to about 10 μM, 15 about 0.5 nM to about 1.0 μM, or about 1.0 nM to about 100 nM.

In still another embodiment, the modified IL-4 mutein receptor antagonist inhibits the proliferative response of TF-1 cells to IL-13 with an $IC_{50}$ selected from about 0.1 nM to about 10 μM, about 0.5 nM to about 1 μM, or about 1.0 nM to about 100 nM.

In a further embodiment, the modified IL-4 mutein receptor antagonist inhibits the proliferative response of human B cells to IL-4 with an $IC_{50}$ selected from about 0.1 nM to about 10 μM, about 0.5 nM to about 1.0 μM, or about 1.0 nM to about 100 nM.

In another embodiment, the modified IL-4 mutein receptor antagonist inhibits the proliferative response of human T cells to IL-4 with an $IC_{50}$ selected from the group consisting of about 0.1 nM to about 10 μM, about 0.5 nM to about 1 μM, about 1.0 nM to about 100 nM.

In yet another embodiment, a modified IL-4 mutein receptor antagonist of the invention has a plasma half-life which is at least about 2-10 fold greater than that of an unmodified IL-4 receptor antagonist.

The invention also provides pharmaceutical compositions comprising: (a) a modified IL-4 mutein receptor antagonist which binds to the human IL-4 receptor; and (b) a pharmaceutically acceptable carrier.

The invention also provides a purified polynucleotide comprising (a) a nucleotide sequence as set forth in SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 31; or (b) a nucleotide sequence encoding a polypeptide having an amino acid sequence as set forth in SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 32, or SEQ ID NO: 33.

The invention also provides expression vectors comprising a polynucleotide of the invention and host cells comprising an expression vector of the invention.

In addition, the invention provides methods of making a modified IL-4 mutein receptor antagonist, comprising the steps of: (a) culturing the host cell described above under conditions whereby the antagonist is expressed; and (b) purifying the antagonist from the host cell culture. In a particular aspect, an antagonist produced by a method of the invention can inhibit IL-4 and IL-13-mediated activity and is coupled to a non-protein polymer selected from the group consisting of polyethylene glycol, polypropylene glycol and polyoxyalkylenes.

The invention also provides methods for treating a human disorder associated with increased activity of IL-4 and IL-13, comprising the steps of: (a) providing a human having a condition in which activity of IL-4 and IL-13 is increased; and (b) administering to said human an effective amount of modified IL-4 mutein receptor antagonist of the invention or a pharmaceutical composition of the invention. In one aspect, the disorder is asthma, chronic obstructive pulmonary disease (such as emphysema or chronic bronchitis), or related pulmonary conditions.

The invention also provides a method of preparing a modified IL-4 mutein receptor antagonist in active form, antagonists prepared by the method, compositions comprising such antagonists and method of treating human disorders comprising administering such antagonists, and pharmaceutical compositions including such antagonists. The method comprises the steps of: (a) culturing the host cell as described above under conditions whereby the antagonist is expressed; (b) allowing the antagonist to refold in the presence of dithiothreitol; and (c) purifying the antagonist from the host cell culture. In one embodiment, the method further comprises the steps of: (d) coupling the antagonist to a non-protein polymer; and (e) purifying the antagonist coupled to the non-protein polymer.

Specific preferred embodiments of the present invention will become evident from the following more detailed description of certain preferred embodiments and the claims.

DETAILED DESCRIPTION OF THE INVENTION

Figure 1:
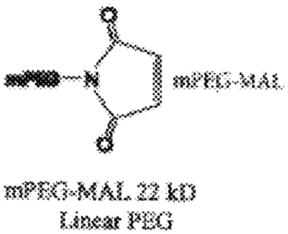
FIG. 1 shows a schematic representation of the chemistry of a PEGylation reaction.
Figure 1:
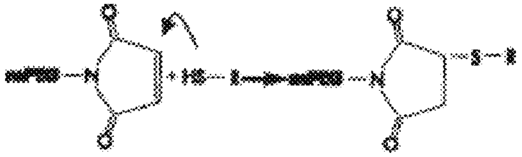

This invention relates to modified IL-4 mutein receptor antagonists comprising an IL-4 mutein receptor coupled to a non-protein polymer, preferably a polyethylene glycol molecule.

Unless otherwise required by context, singular terms shall include pluralities and plural terms shall include the singular.

The section headings used herein are for organizational purposes only and are not to be construed as limiting the subject matter described. All references cited in this application are expressly incorporated by reference herein.

The term "polynucleotide" or "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-5 N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "purified" or "isolated" polynucleotide refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

As used herein, "wild type IL-4" or "wtIL-4" and equivalents thereof are used interchangeably and mean human Interleukin-4, native or recombinant, having the 129 normally occurring amino acid sequence of native human IL-4, as disclosed in U.S. Pat. No. 5,017,691, incorporated herein by reference. Further, the modified human IL-4 receptor antagonists described herein may have various insertions and/or deletions and/or couplings to a non-protein polymer, and are numbered in accordance with the wtIL-4, which means that the particular amino acid chosen is that same amino acid that normally occurs in the wtIL-4. Accordingly, one skilled in the art will appreciate that the normally occurring amino acids at positions, for example, 13 (threonine), 121 (arginine), and/or 124 (tyrosine), may be shifted in the mutein. Thus, an insertion of a cysteine residue at amino acid positions, for example, 38, 102 and/or 104 may be shifted on the mutein. However, the location of the shifted Ser (S), Arg (R), Tyr (Y) or inserted Cys (C) can be determined by inspection and correlation of the flanking amino acids with those flanking Ser, Arg, Tyr or Cys in wtIL-4.

Further, the DNA sequence encoding human IL-4 or a mutant human IL-4 protein may or may not include DNA sequences that encode a signal sequence. Such signal sequence, if present, should be one recognized by the cell chosen for expression of the IL-4 mutein. It may be prokaryotic, eukaryotic or a combination of the two. It may also be the signal sequence of native IL-4. The inclusion of a signal sequence depends on whether it is desired to secrete the IL-4 mutein from the recombinant cells in which it is made. If the chosen cells are prokaryotic, it generally is preferred that the DNA sequence not encode a signal sequence, but include an N-terminal methionine to direct expression. If the chosen cells are eukaryotic, it generally is preferred that a signal sequence be encoded and most preferably that the wild-type IL-4 signal sequence be used, as disclosed in U.S. Pat. No. 6,028,176, incorporated herein by reference.

As used herein, the terms "mutant human IL-4 protein," "modified human IL-4 receptor antagonist," "mhIL-4," "IL-4 mutein," "IL-4 antagonist," and equivalents thereof are used interchangeably and are within the scope of the invention. These polypeptides and functional fragments thereof refer to polypeptides wherein specific amino acid substitutions to the mature human IL-4 protein have been made. These polypeptides include the mIL-4 compositions of the present invention, which are administered to a subject in need of treatment for asthma. In particular, the mhIL-4 of the present invention, include at least the R121D/Y124D pair of substitutions ("IL-4RA") (SEQ ID NO: 31).

As used herein, a "functional fragment" is a polypeptide which has IL-4 antagonistic activity, including smaller peptides. These and other aspects of mhIL-4 and modification of hIL-4 are described in U.S. Pat. Nos. 6,335,426; 6,313,272; and 6,028,176, the entire contents of which are incorporated herein by reference.

By "numbered according to wild type IL-4" we mean identifying a chosen amino acid with reference to the position at which that amino acid normally occurs in wild type IL-4.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "host cell" is used herein to refer to a cell that has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g. Graham et al, 1973, *Virology* 10 52:456; Sambrook et al, *Molecular Cloning, A Laboratory Manual* (Cold Spring Harbor Laboratories, 1989); Davis et al, *Basic Methods in Molecular Biology* (Elsevier, 1986); and Chu et al, 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. “Identity” measures the percent of identical matches between the smaller of two or more sequences with gap alignments (if any) addressed by a particular mathematical model or computer program (i.e., “algorithms”).

The term “similarity” is a related concept, but in contrast to “identity,” “similarity” refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

Identity and similarity of related nucleic acids and polypeptides can be readily calculated by known methods. Such methods include, but are not limited to, those described in COMPUTATIONAL MOLECULAR BIOLOGY, (Lesk, A. M., ed.), 1988, Oxford University Press, New York; BIOCOMPUTING: INFORMATICS AND GENOME PROJECTS, (Smith, D. W., ed.), 1993, Academic Press, New York; COMPUTER ANALYSIS OF SEQUENCE DATA, Part 1, (Griffin, A. M., and Griffin, H. G., eds.), 1994, Humana Press, New Jersey; von Heinje, G., SEQUENCE ANALYSIS IN MOLECULAR BIOLOGY, 1987, Academic Press; SEQUENCE ANALYSIS PRIMER, (Gribskov, M. and Devereux, J., eds.), 1991, M. Stockton Press, New York; Carillo et al, 1988, SIAM J. Applied Math., 48:1073; and Durbin et al, 1998, BIOLOGICAL SEQUENCE ANALYSIS, Cambridge University Press.

Preferred methods to determine identity are designed to give the largest match between the sequences tested. Methods to determine identity are described in publicly available computer programs. Preferred computer program methods to determine identity between two sequences include, but are not limited to, the GCG program package, including GAP (Devereux et al, 1984, Nucl. Acid. Res., 12:387; Genetics Computer Group, University of Wisconsin, Madison, Wis.), BLASTP, BLASTN, and FASTA (Altschul et al, 1990, J. Mol. Biol, 215:403-410). The BLASTX program is publicly available from the National Center for Biotechnology Information (NCBI) and other sources (BLAST Manual, Altschul et al NCB/NLM/NIH Bethesda, Md. 20894; Altschul et al, 1990, supra). The well-known Smith Waterman algorithm may also be used to determine identity.

Certain alignment schemes for aligning two amino acid sequences may result in matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the “matched span”, as determined by the algorithm). In certain embodiments, a gap opening penalty (which is calculated as three-times the average diagonal; where the “average diagonal” is the average of the diagonal of the comparison matrix being used; the “diagonal” is the score or number assigned to each perfect amino acid match by the particular comparison matrix) and a gap extension penalty (which is usually one-tenth of the gap opening penalty), as well as a comparison matrix such as PAM250 or BLOSUM 62 are used in conjunction with the algorithm. In certain embodiments, a standard comparison matrix (see Dayhoff et al, 1978, Atlas of Protein Sequence and Structure, 5:345-352 for the PAM 250 comparison matrix; Henikoff et al, 1992, *Proc. Natl. Acad. Sci. USA,* 89:10915-10919 for the BLOSUM 62 comparison matrix) is also used by the algorithm.

In certain embodiments, the parameters for a polypeptide sequence comparison include the following:

Algorithm: Needleman et al, 1970, *J. Mol. Biol,* 48:443-453;

Comparison matrix: BLOSUM 62 from Henikoff et al, 1992, supra;

Gap Penalty: 12

Gap Length Penalty: 4

Threshold of Similarity: 0

The GAP program may be useful with the above parameters. In certain embodiments, the aforementioned parameters are the default parameters for polypeptide comparisons (along with no penalty for end gaps) using the GAP algorithm.

As used herein, the twenty conventional amino acids and their abbreviations follow conventional usage. See IMMUNOLOGY—A SYNTHESIS, 2nd Edition, (E. S. Golub and D. R. Gren, Eds.), Sinauer Associates: Sunderland, Mass., 1991, incorporated herein by reference for any purpose. Stereoisomers (e.g., D-amino acids) of the twenty conventional amino acids; unnatural amino acids such as α-, α-disubstituted amino acids, N-alkyl amino acids, lactic acid, and other unconventional amino acids may also be suitable components for polypeptides of the invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:

1) hydrophobic: norleucine (Nor), Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Conservative amino acid substitutions may involve exchange of a member of one of these classes with another member of the same class. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Non-conservative substitutions may involve the exchange of a member of one of these classes for a member from another class. Such substituted residues may be introduced into regions of a human protein that are homologous with non-human proteins, or into the non-homologous regions of the molecule.

In making such changes, according to certain embodiments, the hydropathic index of amino acids may be considered. Each amino acid has been assigned a hydropathic index on the basis of its hydrophobicity and charge characteristics.

They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art (see, for example, Kyte et al, 1982, *J. Mol. Biol.* 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gin, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |

TABLE 1-continued

Amino Acid Substitutions

| Original Residues | Exemplary Substitutions | Preferred Substitutions |
|---|---|---|
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar polypeptides. In further embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of a polypeptide with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Op. in Biotech.* 7:422-427; Chou et al, 1974, *Biochemistry* 13:222-245; Chou et al, 1974, *Biochemistry* 113:211-222; Chou et al, 1978, *Adv. Enzymol Relat. Areas Mol. Biol.* 47:45-148; Chou et al, 1979, *Ann. Rev. Biochem.* 47:251-276; and Chou et al, 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al, 1999, *Nucl. Acid. Res.* 27:244-247. It has been suggested (Brenner et al, 1997, *Curr. Op. Struct. Biol.* 7:369-376) that there are a limited number of folds in a given polypeptide or protein and that once a critical number of 5 structures have been resolved, structural prediction will become dramatically more accurate.

Additional methods of predicting secondary structure include "threading" (Jones, 1997, *Curr. Opin. Struct. Biol.* 7:377-87; Sippl et al, 1996, *Structure* 4:15-19), "profile analysis" (Bowie et al, 1991, *Science* 253:164-170; Gribskov et al, 1990, *Meth. Enzym.* 183:146-159; Gribskov et al, 1987, *Proc. Nat. Acad. Sci.* 84:4355-4358), and "evolutionary linkage" (See Holm, 1999, supra; and Brenner, 1997, supra).

In certain embodiments, protein variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred variants include cysteine variants wherein one or more cysteine residues are deleted from or substituted for another amino acid (e.g., serine) compared to the parent amino acid sequence. Cysteine variants may be useful when proteins must be refolded into a biologically active conformation such as after the isolation of insoluble inclusion bodies. Cysteine variants generally have fewer cysteine residues than the native protein, and typically have an even number to minimize interactions resulting from unpaired cysteines.

In additional embodiments, protein variants can include mutations such as substitutions, additions, deletions, or any combination thereof, and are typically produced by site-directed mutagenesis using one or more mutagenic oligonucleotide(s) according to methods described herein, as well as according to methods known in the art (see, for example, Sambrook et al, MOLECULAR CLONING: A LABORATORY MANUAL, 3rd Ed., 2001, Cold Spring Harbor, N.Y. and Berger and Kimmel, METHODS IN ENZYMOLOGY, Volume 152, Guide to Molecular Cloning Techniques, 1987, Academic Press, Inc., San Diego, Calif., which are incorporated herein by reference).

According to certain embodiments, amino acid substitutions are those that: (1) reduce susceptibility to proteolysis, (2) reduce susceptibility to oxidation, (3) alter binding affinity for forming protein complexes, (4) alter binding affinities, and/or (5) confer or modify other physicochemical or functional properties on such polypeptides. According to certain embodiments, single or multiple amino acid substitutions (in certain embodiments, conservative amino acid substitutions) may be made in the naturally occurring sequence (in certain embodiments, in the portion of the polypeptide outside the domain(s) forming intermolecular contacts). In preferred embodiments, a conservative amino acid substitution typically does not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in PROTEINS, STRUCTURES AND MOLECULAR PRINCIPLES, (Creighton, Ed.), 1984, W.H. Freeman and Company, New York; INTRODUCTION TO PROTEIN STRUCTURE (C. Branden and J. Tooze, eds.), 1991, Garland Publishing, New York, N.Y.; and Thornton et al., 1991, Nature 354:105, each of which are incorporated herein by reference.

Peptide analogs are commonly used in the pharmaceutical industry as non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, *TINS* p. 392; and Evans et al, 1987, *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: $-CH_2-NH-$, $-CH_2-S-$, $-CH_2-CH_2-$, $-CH{=}CH-$(cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

In the context of the present invention, the phrase "nucleic acid sequences," when referring to sequences which encode a protein, polypeptide, or peptide, is meant to include degenerative nucleic acid sequences which encode homologous protein, polypeptide or peptide sequences as well as the disclosed sequence.

(a) Characteristics of Modified IL-4 Mutein Receptor Antagonists

"Modified IL-4 mutein receptor antagonists," as used herein, includes the IL-4RA mutein described in U.S. Pat. Nos. 6,028,176 & 6,313,272 (hereby incorporated by reference in their entirety) with additional amino acid substitutions at one or more positions of the mature IL-4 protein. Exemplary triple muteins include, but are not limited to a substitution of arginine by aspartic acid at position 121, of tyrosine by aspartic acid at position 124, and of serine by aspartic acid at position 125 in the D-helix; and a substitution of threonine by aspartic acid at position 13, of arginine by aspartic acid at position 121, and of tyrosine by aspartic acid at position 124 in the D-helix. In one embodiment, the triple muteins further comprise an N-terminal methionine. Variations in this section of the D helix positively correlate with changes in interactions at the second binding region. The modified IL-4 mutein receptor antagonist may further include one or more substitutions wherein said substitutions enable the site-specific coupling of at least one non-protein polymer, such as polypropylene glycol, polyoxyalkylene, or polyethylene glycol (PEG) molecule to the mutein. Site-specific coupling of PEG, for example, allows the generation of a modified mutein which possesses the benefits of a polyethylene-glycosylated (PEGylated) molecule, namely increased plasma half life and decreased immunogenicity while maintaining greater potency over non-specific PEGylation strategies such as N-terminal and lysine side-chain PEGylation.

It should be understood that the structure of the attached PEG moieties is important in optimizing the PEGylation of the muteins of the invention. In one embodiment, the PEG moiety is linear. Linear PEG moieties are limited in size by the manufacturing process because the amount of PEG-diol increases as PEG molecular weight increases. With linear moieties, increases in PEG-mutein molecular size is typically accomplished by increasing the number of PEG attachment sites on the mutein. This often results in suboptimal pharmacological profiles. In another embodiment, the PEG moiety is branched from a single attachment site. Branched PEG moieties have the advantage of increasing the size of the PEG molecule without increasing the number of site attachments.

Thus, in one aspect, the polyethylene glycol (PEG) moiety has a molecular weight ranging from about 3 kD to 50 kD. In one embodiment, the PEG moiety is about 40 kD. Covalent attachment of the PEG to the drug (known as "PEGylation") may be accomplished by known chemical reactions and/or synthesis techniques. For example, in one aspect of the present invention, the PEGylation of protein may be accomplished by reacting NHS-activated PEG with the mutein under suitable reaction conditions. In another aspect of the present invention, the PEGylation of protein may be accomplished by reacting a maleimide activated PEG with the sulfhydryl group of the cytsteine residue in the protein under suitable reaction conditions.

PEG-mutein conjugates can be created in three different ways: A single large PEG moiety can be attached at a single site on the mutein; a branched PEG moiety (i.e., two or more medium PEG chains joined together via a linker) can be attached at a single site on the mutein; or several small chains may be attached at multiple sites on the mutein. Theoretically, monosite PEGylated muteins have higher activity because the PEG attachment is less likely to occur at or near receptor-binding domains.

Improvements in PEGylation and other types of post-translational modifications (PTMs) have been extensive and there are now a large number of PTM techniques and reagents known in the art, and new ones are regularly being developed. Techniques and reagents for PEGylation include, for example: (i) specialized linkers and coupling chemistries; (ii) branched PEGs which effectively allow additional PEG groups to be attached to a single conjugation site; (iii) site-specific PEGylation, including site-specific monoPEGylation; and (iv) site-directed enzymatic PEGylation (e.g. using a transglutaminase reaction). There are also additional technologies and reagents available from an increasing number of commercial suppliers (see, e.g., Nektar/Shearwater (on the world wide web at nektar.com), Sunbio (on the world wide web at sunbio.com and sunbio.com/peg-shop), Celares GmbH (on the world wide web at celares.com), NOF Corporation (on the world wide web at peg-drug.com), and others).

Also included in this invention is the selection of the specific site of amino acid substitution which enables proper folding of the molecule following expression. Modified IL-4 mutein receptor antagonists bind to IL-4 and IL-13 with an affinity loss not greater than 10-fold relative to that of IL-4RA. Modified IL-4 mutein receptor antagonists inhibit IL-4 and IL-13 mediated activity with a loss of potency not greater than 10-fold relative to that of IL-4RA. In addition, modified IL-4 mutein receptor antagonists possess a plasma half-life which is at least 2 to 10-fold greater than that of unmodified IL-4RA.

The IL-4 muteins of this invention may also be characterized by amino acid insertions, deletions, substitutions and modifications at one or more sites in or at the other residues of the native IL-4 polypeptide chain. In accordance with this invention any such insertions, deletions, substitutions and modifications should result in an IL-4 mutein that retains its IL-4-related activity.

An additional aspect of this invention is provided in the method with which the protein is expressed and refolded, as depicted in Example 2. The IL-4 mutein must be purified properly to allow efficient PEGylation. An exemplary method for purification is described in Example 2 below. When the mutein is refolded in the presence of a sulfhydryl protecting agent a covalent disulfide bond is formed between the IL-4 mutein's free cysteine and the protecting agent. In contrast, the use of the sulfhydryl protecting agent dithiothreitol (DTT), which oxidizes to form a stable disulfide bond, will not form a covalent bond with the IL-4 mutein's free cysteine, thus leaving its sulfhydryl group free to react with the PEG maleimide reagent. IL-4 muteins purified after refolding in the presence of a sulfhydryl protecting agent can react with the PEG reagent if treated with DTT, but a mixture of monoPEGylated and multiPEGylated products are generated, suggesting that existing IL-4 cysteines are also PEGylated. PEGylation of existing cysteines would lead to misfolded products that are inactive.

The $K_D$ of modified IL-4 mutein receptor antagonists to the IL-4 receptor can be assayed using any method known in the art, including technologies such as real-time Bimolecular Interaction Analysis (BIA) outlined in Example 4. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

The capacity of modified IL-4 mutein receptor antagonists to inhibit the proliferative response of immune cells can be assessed using proliferative assays as outlined in Example 5 and this capacity expressed as an Inhibitory Concentration 50% ($IC_{50}$).

In a BIAcore™ assay, modified IL-4 mutein receptor antagonists of the present invention specifically bind to the human IL-4 receptor with a preferred $K_D$ in the range of from about 1.0 nM to about 100 nM. More preferred embodiments of the present invention bind to human IL-4 receptor with a $K_D$ of approximately 0.5 nM to about 1.0 uM. Still more preferred embodiments of the present invention bind to human IL-4 receptor with a $K_D$ of approximately 0.1 nM to about 10 μM. Additionally, modified IL-4 mutein receptor antagonists of the present invention, as envisioned, will bind to human IL-4 receptor and neutralize its capacity to promote immune cell proliferation with a preferred $IC_{50}$ ranging from about 1.0 nM to about 100 nM. More preferred human antagonists bind IL-4 receptor and neutralize its immune cell proliferation capacity with an $IC_{50}$ ranging from approximately 0.5 nM to 1 μM with the most preferred antagonists of this invention binding and inhibiting IL-4 receptor with an $IC_{50}$ of approximately 0.1 nM to about 10 μM.

The current embodiments of modified IL-4 mutein receptor antagonists of the present invention also exhibit a plasma half-life that is preferably at least 2 to 10-fold greater than that of unmodified IL4RA with the most preferred embodiments of the present invention exhibiting a plasma half-life which is 10-100-fold greater than that of unmodified IL-4RA (see Example 7).

A number of modified IL-4 mutein receptor antagonists with the characteristics described above have been identified by screening candidates with the above assays. The embodiments of the present invention have the polypeptide sequences shown in Table 2 (SEQ ID NOS: 10-16 and 32-33).

TABLE 2

Polypeptide Sequences

| SEQ ID NO | Name | Sequence |
|---|---|---|
| 9 | IL-4RA (IL-4DM) | MHKCDITLQEIIKTLNSLTEQKTLCTELTVTDIF<br>AASKNTTEKETFCRAATVLRQFYSHHEKDTRCLG<br>ATAQQFHRIKQLIRFLKRLDRNLWGLAGLNSCPV<br>KEANQSTLENFLERLKTIMDEKDSKCSS |
| 10 | IL4-RE-T28C | MHKCDITLQEIIKTLNSLTEQKTLCTELCVTDIF<br>AASKNTTEKETFCRAATVLRQFYSHHEKDTRCLG<br>ATAQQFHRHKQLIRFLKRLDRNLWGLAGLNSCPV<br>KEANQSTLENFLERLKTIMDEKDSKCSS |
| 11 | IL4-RE-S36C | MHKCDITLQEIIKTLNSLTEQKTLCTELTVTDIF<br>AACKNTTEKETFCRAATVLRQFYSHHEKDTRCLG<br>ATAQQFHRHKQLIRFLKRLDRNLWGLAGLNSCPV<br>KEANQSTLENFLERLKTIMDEKDSKCSS |
| 12 | IL4-RE-K37C | MHKCDITLQEIIKTLNSLTEQKTLCTELTVTDIF<br>AASCNTTEKETFCRAATVLRQFYSHHEKDTRCLG<br>ATAQQFHRHKQLIRFLKRLDRNLWGLAGLNSCPV<br>KEANQSTLENFLERLKTIMDEKDSKCSS |
| 13 | IL4-RE-N38C | MHKCDITLQEIIKTLNSLTEQKTLCTELTVTDIF<br>AASKCTTEKETFCRAATVLRQFYSHHEKDTRCLG<br>ATAQQFHRHKQLIRFLKRLDRNLWGLAGLNSCPV<br>KEANQSTLENFLERLKTIMDEKDSKCSS |
| 14 | IL4-RE-A104C | MHKCDITLQEIIKTLNSLTEQKTLCTELTVTDIF<br>AASKNTTEKETFCRAATVLRQFYSHHEKDTRCLG<br>ATAQQFHRHKQLIRFLKRIDRNLWGLAGLNSCPV<br>KECNQSTLENFLERLKTIMDEKDSKCSS |
| 15 | IL4-RE-N105C | MHKCDITLQEIIKTLNSLTEQKTLCTELTVTDIF<br>AASKNTTEKETFCRAATVLRQFYSHHEKDTRCLG<br>ATAQQFHRHKQLIRFLKRIDRNLWGLAGLNSCPV<br>KEACQSTLENFLERLKTIMDEKDSKCSS |
| 16 | IL4-RE-Q106C | MHKCDITLQEIIKTLNSLTEQKTLCTELTVTDIF<br>AASKNTTEKETFCRAATVLRQFYSHHEKDTRCLG<br>ATAQQFHRHKQLIRFLKRIDRNLWGLAGLNSCPV<br>KEANCSTLENFLERLKTIMDEKDSKCSS |
| 32 | IL4-RE-T13D | MHKCDITLQEIIKDLNSLTEQKTLCTELTVTDIF<br>AASKNTTEKETFCRAATVLRQFYSHHEKDTRCLG<br>ATAQQFHRIKQLIRFLKRLDRNLWGLAGLNSCPV<br>KEANQSTLENFLERLKTIMDEKDSKCSS |
| 33 | IL4-RE-T13D-N38C | MHKCDITLQEIIKDLNSLTEQKTLCTELTVTDIF<br>AASKCTTEKETFCRAATVLRQFYSHHEKDTRCLG<br>ATAQQFHRHKQLIRFLKRIDRNLWGLAGLNSCPV<br>KEANQSTLENFLERIKTIMDEKDSKCSS |

(b) Polynucleotides Encoding Modified IL-4 Mutein Receptor Antagonists

The invention also provides polynucleotides encoding modified IL-4 mutein receptor antagonists. These polynucleotides can be used, for example, to produce quantities of the antagonists for therapeutic use. The invention further provides degenerative DNA sequences that encode the same modified IL-4 mutein receptor antagonists. Methods of constructing and expressing degenerative DNA sequences capable of expressing the same amino acid sequence as a given polynucleotide sequence are known in the art.

A polynucleotide of the invention can be readily obtained in a variety of ways including, without limitation, chemical synthesis, cDNA or genomic library screening, expression library screening, and/or PCR amplification of cDNA.

Recombinant DNA methods described herein are generally those set forth in Sambrook et al, *Molecular Cloning: A Laboratory Manual* (Cold Spring Harbor Laboratory Press, 1989) and/or Current Protocols in Molecular Biology (Ausubel et al, eds., Green Publishers Inc. and Wiley and Sons 1994). The invention provides for nucleic acid molecules as described herein and methods for obtaining such molecules.

One method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of a modified IL-4 mutein receptor antagonist cDNA, are then added to the cDNA along with a polymerase such as Taq polymerase, and the polymerase amplifies the cDNA region between the two primers.

Another means of preparing a nucleic acid molecule of the invention is chemical synthesis using methods well known to the skilled artisan such as those described by Engels et al, 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA will be several hundred nucleotides in length. Nucleic acids larger than about 100 nucleotides can be synthesized as several fragments using these methods. The fragments can then be ligated together. Other methods known to the skilled artisan may be used as well.

Polynucleotides of the invention that can be used to encode the modified IL-4 mutein receptor antagonists are shown in Table 3 (SEQ ID NOs: 2-8 and 31).

TABLE 3

Polynucleotide Sequences

| SEQ ID NO | Name | Sequence |
|---|---|---|
| 1 | IL-4RA | ATGCACAAGTGCGATATCACCTTACAGGAGATC<br>ATCAAAACTTTGAACAGCCTCACAGAGCAGAA<br>GACTCTGTGCACCGAGTTGACCGTAACAGACAT<br>CTTTGCTGCCTCCAAGAACACAACTGAGAAGGA<br>AACCTTCTGCAGGGCTGCGACTGTGCTCCGGCA<br>GTTCTACAGCCACCATGAGAAGGACACTCGCTG<br>CCTGGGTGCGACTGCACAGCAGTTCCACAGGCA<br>CAAGCAGCTGATCCGATTCCTGAAACGGCTCGA<br>CAGGAACCTCTGGGGCCTGGCGGGCTTGAATTC<br>CTGTCCTGTGAAGGAAGCCAACCAGAGTACGTT<br>GGAAAACTTCTTGGAAAGGCTAAAGACGATCAT<br>GGACGAGAAAGACTCAAAGTGTTCGAGCTAAT<br>AA |
| 2 | IL4-RE-T28C | ATGCACAAGTGCGATATCACCTTACAGGAGAT<br>CATCAAAACTTTGAACAGCCTCACAGAGCAGA<br>AGACTCTGTGCACCGAGTTGTGCGTAACAGAC<br>ATCTTTGCTGCCTCCAAGAACACAACTGAGAA<br>GGAAACCTTCTGCAGGGCTGCGACTGTGCTCC<br>GGCAGTTCTACAGCCACCATGAGAAGGACACT<br>CGCTGCCTGGGTGCGACTGCACAGCAGTTCCA<br>CAGGCACAAGCAGCTGATCCGATTCCTGAAAC<br>GGCTCGACAGGAACCTCTGGGGCCTGGCGGGC<br>TTGAATTCCTGTCCTGTGAAGGAAGCCAACCA |

TABLE 3-continued

Polynucleotide Sequences

| SEQ ID NO | Name | Sequence |
|---|---|---|
| | | GAGTACGTTGGAAAACTTCTTGGAAAGGCTAA<br>AGACGATCATGGACGAGAAAGACTCAAAGTGT<br>TCGAGCTAATAA |
| 3 | IL4-RE-S36C | ATGCACAAGTGCGATATCACCTTACAGGAGAT<br>CATCAAAACTTTGAACAGCCTCACAGAGCAGA<br>AGACTCTGTGCACCGAGTTGACCGTAACAGAC<br>ATCTTTGCTGCCTGCAAGAACACAACTGAGAA<br>GGAAACCTTCTGCAGGGCTGCGACTGTGCTCC<br>GGCAGTTCTACAGCCACCATGAGAAGGACACT<br>CGCTGCCTGGGTGCGACTGCACAGCAGTTCCA<br>CAGGCACAAGCAGCTGATCCGATTCCTGAAAC<br>GGCTCGACAGGAACCTCTGGGGCCTGGCGGGC<br>TTGAATTCCTGTCCTGTGAAGGAAGCCAACCA<br>GAGTACGTTGGAAAACTTCTTGGAAAGGCTAA<br>AGACGATCATGGACGAGAAAGACTCAAAGTGT<br>TCGAGCTAATAA |
| 4 | IL4-RE-K37C | ATGCACAAGTGCGATATCACCTTACAGGAGAT<br>CATCAAAACTTTGAACAGCCTCACAGAGCAGA<br>AGACTCTGTGCACCGAGTTGACCGTAACAGAC<br>ATCTTTGCTGCCTCCTGCAACACAACTGAGAA<br>GGAAACCTTCTGCAGGGCTGCGACTGTGCTCC<br>GGCAGTTCTACAGCCACCATGAGAAGGACACT<br>CGCTGCCTGGGTGCGACTGCACAGCAGTTCCA<br>CAGGCACAAGCAGCTGATCCGATTCCTGAAAC<br>GGCTCGACAGGAACCTCTGGGGCCTGGCGGGC<br>TTGAATTCCTGTCCTGTGAAGGAAGCCAACCA<br>GAGTACGTTGGAAAACTTCTTGGAAAGGCTAA<br>AGACGATCATGGACGAGAAAGACTCAAAGTGT<br>TCGAGCTAATAA |
| 5 | IL4-RE-N38C | ATGCACAAGTGCGATATCACCTTACAGGAGAT<br>CATCAAAACTTTGAACAGCCTCACAGAGCAGA<br>AGACTCTGTGCACCGAGTTGACCGTAACAGAC<br>ATCTTTGCTGCCTCCAAGTGCACAACTGAGAA<br>GGAAACCTTCTGCAGGGCTGCGACTGTGCTCC<br>GGCAGTTCTACAGCCACCATGAGAAGGACACT<br>CGCTGCCTGGGTGCGACTGCACAGCAGTTCCA<br>CAGGCACAAGCAGCTGATCCGATTCCTGAAAC<br>GGCTCGACAGGAACCTCTGGGGCCTGGCGGGC<br>TTGAATTCCTGTCCTGTGAAGGAAGCCAACCA<br>GAGTACGTTGGAAAACTTCTTGGAAAGGCTAA<br>AGACGATCATGGACGAGAAAGACTCAAAGTGT<br>TCGAGCTAATAA |
| 6 | IL4-RE-A104C | ATGCACAAGTGCGATATCACCTTACAGGAGAT<br>CATCAAAACTTTGAACAGCCTCACAGAGCAGA<br>AGACTCTGTGCACCGAGTTGACCGTAACAGAC<br>ATCTTTGCTGCCTCCAAGAACACAACTGAGAA<br>GGAAACCTTCTGCAGGGCTGCGACTGTGCTCC<br>GGCAGTTCTACAGCCACCATGAGAAGGACACT<br>CGCTGCCTGGGTGCGACTGCACAGCAGTTCCA<br>CAGGCACAAGCAGCTGATCCGATTCCTGAAAC<br>GGCTCGACAGGAACCTCTGGGGCCTGGCGGGC<br>TTGAATTCCTGTCCTGTGAAGGAATGCAACCA<br>GAGTACGTTGGAAAACTTCTTGGAAAGGCTAA<br>AGACGATCATGGACGAGAAAGACTCAAAGTGT<br>TCGAGCTAATAA |
| 7 | IL4-RE-N105C | ATGCACAAGTGCGATATCACCTTACAGGAGAT<br>CATCAAAACTTTGAACAGCCTCACAGAGCAGA<br>AGACTCTGTGCACCGAGTTGACCGTAACAGAC<br>ATCTTTGCTGCCTCCAAGAACACAACTGAGAA<br>GGAAACCTTCTGCAGGGCTGCGACTGTGCTCC<br>GGCAGTTCTACAGCCACCATGAGAAGGACACT<br>CGCTGCCTGGGTGCGACTGCACAGCAGTTCCA<br>CAGGCACAAGCAGCTGATCCGATTCCTGAAAC<br>GGCTCGACAGGAACCTCTGGGGCCTGGCGGGC<br>TTGAATTCCTGTCCTGTGAAGGAAGCCTGCCA<br>GAGTACGTTGGAAAACTTCTTGGAAAGGCTAA<br>AGACGATCATGGACGAGAAAGACTCAAAGTGT<br>TCGAGCTAATAA |

TABLE 3-continued

Polynucleotide Sequences

| SEQ ID NO | Name | Sequence |
|---|---|---|
| 8 | 1L4-RE-Q106C | ATGCACAAGTGCGATATCACCTTACAGGAGAT<br>CATCAAAACTTTGAACAGCCTCACAGAGCAGA<br>AGACTCTGTGCACCGAGTTGACCGTAACAGAC<br>ATCTTTGCTGCCTCCAAGAACACAACTGAGAA<br>GGAAACCTTCTGCAGGGCTGCGACTGTGCTCC<br>GGCAGTTCTACAGCCACCATGAGAAGGACACT<br>CGCTGCCTGGGTGCGACTGCACAGCAGTTCCA<br>CAGGCACAAGCAGCTGATCCGATTCCTGAAAC<br>GGCTCGACAGGAACCTCTGGGGCCTGGCGGGC<br>TTGAATTCCTGTCCTGTGAAGGAAGCCAACTG<br>CAGTACGTTGGAAAACTTCTTGGAAAGGCTAA |
| 31 | IL4-RE-T13D-N38C (IL-4TM-N38C) | ATGCACAAATGCGATATCACCCTGCAGGAAATC<br>ATCAAAGACCTGAATTCTCTGACCGAACAGAAA<br>ACCCTGTGCACCGAACTGACCGTTACCGACATC<br>TTCGCTGCTTCGAAATGCACCACCGAAAAAGAA<br>ACCTTCTGCCGTGCTGCTACCGTTCTGCGTCAGT<br>TCTACTCTCACCACGAAAAAGACACCCGTTGCC<br>TGGGTGCTACCGCTCAGCAGTTCCACCGTCACA<br>AACAGCTGATCCGTTTCCTGAAACGTCTGGACC<br>GTAACCTGTGGGGTCTGGCTGGTCTGAACAGCT<br>GCCCGGTTAAAGAAGCTAACCAGTCTACCCTGG<br>AAAACTTCCTGGAACGTCTGAAAACCATCATGG<br>ACGAAAAAGACTCTAAATGCTCTTCT |

The invention also provides expression vectors comprising a polynucleotide of the invention and host cells comprising an expression vector of the invention.

A polynucleotide of the invention can be inserted into an appropriate expression vector using standard ligation techniques. The vector is typically selected to be functional in the particular host cell employed (i.e., the vector is compatible with the host cell machinery such that amplification of the gene and/or expression of the gene can occur). A polynucleotide of the invention may be expressed in prokaryotic, yeast, insect (baculovirus systems) and/or eukaryotic host cells. Selection of the host cell will depend on various factors, such as desired expression levels. For a review of expression vectors, see *Meth. Enz.*, vol. 185 (D. V. Goeddel, ed., Academic Press 1990).

Typically, expression vectors used in a host cell will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate IL-4 mutein receptor antagonist expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the IL-4 mutein receptor antagonist gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a modified IL-4 mutein receptor antagonist. As a result, increased quantities of a modified IL-4 mutein receptor antagonist are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a modified IL-4 mutein receptor antagonist. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a modified IL-4 mutein receptor antagonist out of a host cell. Typically, a nucleotide sequence encoding the signal sequence is positioned in the coding region of a modified IL-4 mutein receptor antagonist nucleic acid molecule, or directly at the 5' end of a modified IL-4 mutein receptor antagonist coding region. Many signal sequences have been identified, and any of those that are functional in the selected host cell may be used in conjunction with a modified IL-4 mutein receptor antagonist nucleic acid molecule. Therefore, a signal sequence may be homologous (naturally occurring) or heterologous to the modified IL-4 mutein receptor antagonist nucleic acid molecule. Additionally, a signal sequence may be chemically synthesized using methods described herein. In most cases, the secretion of a modified IL-4 mutein receptor antagonist from the host cell via the presence of a signal peptide will result in the removal of the signal peptide from the secreted modified IL-4 mutein receptor antagonist. The signal sequence may be a component of the vector, or it may be a part of a modified IL-4 mutein receptor antagonist nucleic acid molecule that is inserted into the vector.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the modified IL-4 mutein receptor antagonist gene especially where the gene used is a full-length genomic sequence or a fragment thereof. If the intron is not naturally occurring within the gene, the intron can be obtained from another source. The position of the intron with respect to flanking sequences and the modified IL-4 mutein receptor antagonist gene is generally important, as the intron must be transcribed to be effective. Thus, when a nucleic acid molecule of the invention is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron can be used in the vector.

The expression and cloning vectors of the present invention will typically contain a promoter that is recognized by the host organism and operably linked to the nucleic acid molecule of the invention. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter can be operably linked to a nucleic acid molecule of the invention by removing the promoter from the source DNA by restriction enzyme digestion and inserting the desired promoter sequence into the vector. The native IL-4 mutein receptor antagonist promoter sequence can be used to direct amplification and/or expression of a nucleic acid molecule of the invention. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al, 1980, *Cell* 22:787-97); the herpes thymidine kinase promoter (Wagner et al, 1981, *Proc. Natl. Acad. Sci. U.S.A.* 78:1444-45); the regulatory sequences of the metallothionine gene (Brinster et al, 1982, *Nature* 296:39-42); prokaryotic expression vectors such as the beta-lactamase promoter (Villa-Kamaroff et al, 1978, *Proc. Natl. Acad. Sci. U.S.A.,* 75:3727-31); or the tac promoter (DeBoer et al, 1983, *Proc. Natl. Acad. Sci. U.S.A.,* 80:21-25). Also of interest are the following animal transcriptional control regions, which exhibit tissue specificity and have been utilized in transgenic animals: the elastase I gene control region which is active in pancreatic acinar cells (Swift et al, 1984, *Cell* 38:639-46; Ornitz et al, 1986, *Cold Spring Harbor Symp. Quant. Biol* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al, 1984, *Cell* 38:647-58; Adames et al, 1985, *Nature* 318:533-38; Alexander et al, 1987, *Mol. Cell. Biol,* 7:1436-44); the mouse mammary tumor virus control region which is active in testicular, breast, lymphoid and mast cells (Leder et al, 1986, *Cell* 45:485-95); the albumin gene control region which is active in liver (Pinkert et al, 1987, *Genes and Devel* 1:268-76); the alpha-feto-protein gene control region which is active in liver (Krumlauf et al, 1985, *Mol. Cell. Biol,* 5:1639-48; Hammer et al, 1987, *Science* 235:53-58); the alpha 1-antitrypsin gene control region which is active in the liver (Kelsey et al, 1987, *Genes and Devel.* 1: 161-71); the beta-globin gene control region which is active in myeloid cells (Mogram et al, 1985, *Nature* 315: 338-40; Kollias et al, 1986, *Cell* 46:89-94); the myelin basic protein gene control region which is active in oligodendrocyte cells in the brain (Readhead et al, 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al, 1986, *Science* 234: 1372-78).

An enhancer sequence can be inserted into the vector to increase the transcription of a nucleic acid molecule of the invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule of the invention, it is typically located at a site 5' from the promoter.

Expression vectors of the invention can be constructed from a starting vector such as a commercially available vector. Such vectors may or may not contain all of the desired flanking sequences. Where one or more of the flanking sequences described herein are not already present in the vector, they can be individually obtained and ligated into the vector. Methods used for obtaining each of the flanking sequences are well known to one skilled in the art.

Preferred vectors for practicing this invention are those that are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but one of skill in the art will recognize that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule of the invention has been inserted into the proper site of the vector, the completed vector can be inserted into a suitable host cell for amplification and/or polypeptide expression. The transformation of an expression vector of the invention into a selected host cell can be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al, supra.

Host cells may be prokaryotic host cells (such as *E. coli*) or eukaryotic host cells (such as a yeast, insect, or vertebrate cell). The host cell, when cultured under appropriate conditions, synthesizes a modified IL-4 mutein receptor antagonist that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al, 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g. HB101, DH5D, DH10, and MCI061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al, 1993, *Biotechniques*, 14:810-17; Lucklow, 1993, *Curr. Opin. Biotechnol.* 4:564-72; and Lucklow et al, 1993, *J. Virol.*, 67:4566-79. Preferred insect cells are Sf-9 and Hi5 (Invitrogen).

Polynucleotides of the invention present in a host cell can be isolated free of other cellular components such as membrane components, proteins, and lipids. Polynucleotides can be isolated from cells using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated polynucleotides encoding antagonists of the invention. For example, restriction enzymes and probes can be used to isolate polynucleotides which encode the antagonists. Preferably, isolated polynucleotides are in preparations that are free or at least 70, 80, or 90% free of other molecules.

It will be appreciated by those skilled in the art that the nucleic acid and polypeptide molecules described herein may be produced by recombinant and other means. For example, modified IL-4 mutein receptor antagonist cDNA molecules of the invention can be made with standard molecular biology techniques, using mRNA as a template. Thereafter, cDNA molecules can be replicated using molecular biology techniques known in the art and described in Example 1. Example 2 describes the 5 specific recombinant expression and purification techniques employed in generating the modified mutein antagonists of the invention.

(c) Assessment of Therapeutic Utility of Human Antagonists

To assess the potential efficacy of a particular antagonist in allergic asthma therapy, the antagonist can be tested in vitro in cell proliferation assays as detailed in Examples 5 and 6. In addition, the plasma half-life of the modified IL-4 mutein receptor antagonist can be measured in vivo with a rat pharmacokinetic study according to Example 6.

(d) Pharmaceutical Compositions

Any of the modified IL-4 mutein receptor antagonists described above can be provided in a pharmaceutical composition comprising a pharmaceutically acceptable carrier. The pharmaceutically acceptable carrier preferably is non-pyrogenic. The compositions can be administered alone or in combination with at least one other agent, such as stabilizing compound, which can be administered in any sterile, biocompatible pharmaceutical carrier, including, but not limited to, saline, buffered saline, dextrose, and water. A variety of aqueous carriers may be employed, e.g. 0.4% saline, 0.3% glycine, and the like. These solutions are sterile and generally free of particulate matter. These solutions may be sterilized by conventional, well-known sterilization techniques (e.g., filtration).

The compositions may contain pharmaceutically acceptable auxiliary substances as required. Acceptable auxiliary substances preferably are nontoxic to recipients at the dosages and concentrations employed. The pharmaceutical composition can contain auxiliary substances for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See Remington's Pharmaceutical Sciences (18th Ed., A. R. Gennaro, ed., Mack Publishing Company 1990.

The concentration of the antagonist of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected. If desired, more than one type of antagonist, for example with different $K_D$ for IL-4 receptor binding, can be included in a pharmaceutical composition.

The compositions can be administered to a patient alone, or in combination with other agents, drugs or hormones. In addition to the active ingredients, these pharmaceutical compositions can contain suitable pharmaceutically acceptable carriers comprising excipients and auxiliaries that facilitate processing of the active compounds into preparations which can be used pharmaceutically.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See Remington's Pharmaceutical Sciences (18th Ed., A. R. Gennaro, ed., Mack Publishing Company 1990.

The optimal pharmaceutical composition can be determined by a skilled artisan depending upon, for example, the intended route of administration, delivery format, and desired dosage. See, e.g., Remington's Pharmaceutical Sciences, supra. Such compositions can influence the physical state, stability, rate of in vivo release, and rate of in vivo clearance of the nucleic acid molecule or bone density modulator of the invention.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the invention, pharmaceutical compositions of the invention can be prepared for storage by mixing the selected composition having the desired degree of purity with optional formulation agents (Remington's Pharmaceutical Sciences, supra) in the form of a lyophilized cake or an aqueous solution. Further, the composition can be formulated as a lyophilizate using appropriate excipients such as sucrose.

The pharmaceutical compositions can be selected for parenteral delivery. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in the invention can be in the form of a pyrogen-free, parenterally acceptable, aqueous solution comprising the desired molecule of the invention in a pharmaceutically acceptable vehicle. A particularly suitable vehicle for parenteral injection is sterile distilled water in which the molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid can also be used, which can have the effect of promoting sustained duration in the circulation. Other suitable means for the introduction of the desired molecule include implantable drug delivery devices.

In one embodiment, a pharmaceutical composition can be formulated for inhalation. For example, a nucleic acid molecule or bone density modulator of the invention can be formulated as a dry powder for inhalation. Inhalation solutions can also be formulated with a propellant for aerosol delivery. In yet another embodiment, solutions can be nebulized. Pulmonary administration is further described in PCT Pub. No. WO 94/20069, which describes the pulmonary delivery of chemically modified proteins.

In other embodiments, certain formulations can be administered orally. In one embodiment of the invention, nucleic acid molecules or bone density modulators of the invention that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the molecule or modulator of the invention. Diluents, flavorings, low melting point waxes, vegetable oils, lubricants, suspending agents, tablet disintegrating agents, and binders may also be employed.

Another pharmaceutical composition can involve an effective quantity of nucleic acid molecules or bone density modulators of the invention in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving nucleic acid molecules or bone density modulators of the invention in sustained- or controlled-delivery formulations. Techniques for formulating a variety of other sustained- or controlled-delivery means, such as liposome carriers, bioerodible microparticles or porous beads and depot injections, are also known to those skilled in the art. See, e.g., PCT/US93/00829, which describes the controlled 5 release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al, 1983, *Biopolymers* 22:547-56), poly(2-hydroxyethyl-methacrylate) (Langer et al, 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent No. 133988). Sustained-release compositions may 15 also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

A pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Pharmaceutical compositions of the invention can be administered by any number of routes as described herein including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means.

After pharmaceutical compositions have been prepared, they can be placed in an appropriate container and labeled for treatment of an indicated condition. Such labeling would include amount, frequency, and method of administration.

(d) Therapeutic Methods

The present invention provides methods of ameliorating symptoms of a disorder by binding the IL-4 receptor alpha chain and inhibiting IL-4 and IL-13-mediated activity. These disorders include, without limitation, airway hyperresponsiveness and airway inflammation including, mast cell, eosinophil and lymphocyte, recruitment and activation associated with asthma and other immunological or allergic disorders.

In one embodiment of the invention, a therapeutically effective dose of a modified IL-4 mutein receptor antagonist of the invention and/or a pharmaceutical composition of the invention is administered to a patient having a disorder characterized by elevated IL-4 and IL-13 activity such as those disorders above.

(e) Determination of a Therapeutically Effective Dose

The determination of a therapeutically effective dose is well within the capability of those skilled in the art. A therapeutically effective dose refers to the amount of antagonist that is used to effectively treat asthma compared with the efficacy that is evident in the absence of the therapeutically effective dose.

The therapeutically effective dose can be estimated initially in animal models, usually rats, mice, rabbits, dogs, pigs or non-human primates. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population) of a human antagonist, can be determined by standard pharmaceutical procedures in cell cultures of experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the patient who requires treatment. Dosage and administration are adjusted to provide sufficient levels of the antagonist or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Polynucleotides encoding modified IL-4 mutein receptor antagonists of the invention can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antagonist are in the range of about 5 μg to about 50 μg/kg, about 50 μg to about 5 mg/kg, about 100 μg to about 500 μg/kg of patient body weight, and about 200 to about 250 μg/kg of patient body weight. For administration of polynucleotides encoding the antagonists, effective in vivo dosages are in the range of about 100 ng to about 200 ng, 500 ng to about 50 mg, about 1 μg to about 2 mg, about 5 μg to about 500 μg, and about 20 μg to about 100 μg of DNA.

The mode of administration of modified IL-4 mutein receptor antagonist-containing pharmaceutical compositions of the invention can be any suitable route which delivers the antagonist to the host. Pharmaceutical compositions of the invention are particularly useful for parenteral administration, i.e., subcutaneous, intramuscular, intravenous, intracheal or intranasal and other modes of pulmonary administration.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Recombinant Production of IL-4-RA and IL-4-RE Cysteine Muteins

The pET Directional TOPO® expression system (Invitrogen) was selected for recombinant expression of IL-4. The system uses a highly efficient one-step "TOPO® Cloning" strategy to directionally clone a blunt-end PCR product and a T7lac promoter for high-level and IPTG-inducible expression of the gene of interest in *E. coli*. Additional features include a lacI gene to reduce basal transcription, a pBR322 origin for replication and maintenance of the plasmid and an ampicillin resistance gene for selection.

IL-4 was cloned into pET101/D-TOPO vector for production of recombinant IL-4 protein. The oligonucleotide primers are shown in Table 4. The forward PCR primer was designed with a 5'CACC overhang to facilitate directional cloning, followed by a unique NdeI restriction enzyme site for subcloning and the initial ATG start codon. The reverse PCR primer included two stop codons to make sure no c-terminal tags were incorporated and a unique BamHI restriction enzyme site for subcloning. A blunt-end IL-4 PCR product was generated using previously cloned human IL-4 as a template. The product was gel purified and incubated with salt solution and TOPO® vector for 5 minutes at room temperature to allow for directionally cloning into the pET101/D-TOPO vector. The recombinant vector was transformed into chemically competent One Shot TOP 10 *E. coli*. The recombinant plasmid DNA was sent out for DNA sequencing to confirm the correct sequence.

TABLE 4

Oligonucleotide primers for generating IL-4 RE cysteine muteins

| SEQ ID NO | Oligos for IL4 RE | Sequence |
|---|---|---|
| 17 | T28C Fwd | GAAGACTCTGTGCACCGAGTTGTGCGTAACAGACATCTTTGC |
| 18 | T28C Rev | GCAAAGATGTCTGTTACGCACAACTCGGTGCACAGAGTCTTC |
| 19 | S36C Fwd | GTAACAGACATCTTTGCTGCCTGCAAGAACACAACTGAG |
| 20 | S36C Rev | CTCAGTTGTGTTCTTGCAGGCAGCAAAGATGTCTGTTAC |
| 21 | K37C Fwd | CCGTAACAGACATCTTTGCTGCCTCCTGCAACACAACTGAGAAGG |
| 22 | K37C Rev | CCTTCTCAGTTGTGTTGCAGGAGGCAGCAAAGATGTCTGTTACGG |
| 23 | N38C Fwd | GACATCTTTGCTGCCTCCAAGTGCACAACTGAGAAGGAAACC |
| 24 | N38C Rev | GGTTTCCTTCTCAGTTGTGCACTTGGAGGCAGCAAAGATGTC |
| 25 | A104C Fwd | GAATTCCTGTCCTGTGAAGGAATGCAACCAGAGTACGTTGG |
| 26 | A104C Rev | CCAACGTACTCTGGTTGCATTCCTTCACAGGACAGGAATTC |
| 27 | N105C Fwd | CCTGTGAAGGAAGCCTGCCAGAGTACGTTGGAAAACTTC |
| 28 | N105C Rev | GAAGTTTTCCAACGTACTCTGGCAGGCTTCCTTCACAGG |
| 29 | Q106CFwd | CCTGTCCTGTGAAGGAAGCCAACTGCAGTACGTTGGAAAACTTC |
| 30 | Q106C Rev | GAAGTTTTCCAACGTACTGCAGTTGGCTTCCTTCACAGGACAGG |

IL-4/pET101/D-TOPO served as a template for producing IL-4 RE cysteine muteins with the QuikChange® Site-Directed Mutagenesis Kit from Strategene. Each cysteine mutein was made using two oligonucleotide primers, each complementary to opposite strands of the vector and containing the codon TGC or GC A to incorporate the desired cysteine mutation. Table 4 lists the primers used for producing the IL-4 RE muteins. A mutated plasmid containing staggered nicks was generated using cycling parameters and conditions defined in the manufacturer's protocol. The product was treated with Dpn1 endonuclease for 1 hour at 37° C. to digest the methylated, non-mutated parental DNA template. The DpnI-treated DNA was transformed into XL-1 Blue supercompetent cells where nicks in the mutated plasmid were repaired. The mutagenic 5 plasmid DNA was analysed according to standard sequencing techniques to confirm the correct sequence.

EXAMPLE 2

Recombinant Expression & Purification

BL21 Star (DE3) One Shot cells (Invitrogen) transformed with the protein containing plasmids were characterized for optimal expression and grown at 37° C. until $OD_{600}$ reached approximately 0.4 and induced by 1 mM IPTG (Invitrogen) for 3 hours at 37° C. One liter of cells were pelleted at 13,000 rpm for 10 minutes, weighed and stored at −80° C. The frozen cell pellet was resuspended in 8 ml cell disruption buffer (0.1 M phosphate buffer pH 7.3, 0.1% Triton X100, 1 mM EDTA) per gram of cells and sonicated 4× for 1 minute with 1 minute intervals. The cell lysate was removed by centrifugation at 35,000 g for 10 minutes. The cell pellets were then washed 2-3× by resuspension in 30 ml of cell disruption buffer, by sonication for 1 minute, followed by centrifugation. The final cell pellet, inclusion bodies, was stored at −20° C. Inclusion bodies were resuspended in 5 ml solubilization buffer (0.2M Tris pH 9, 7M guanidine hydrochloride) per gram of cells. Sulphotolysis reagents (0.16 grams sodium sulfite, 0.08 gram potassium tetrathionate per gram of cells) were added and the inclusion bodies were stirred at room temperature for 2 hours. Undissolved constituents were then removed by centrifugation at 35,000 g for 20 minutes leaving solubilized inclusion bodies. The inclusion bodies were then run on a Superdex200 size exclusion column (Akta) to isolate the protein. The column was equilibrated with 2 column volume (CV) of 6M guanidine hydrochloride/PBS pH 7 at a flow rate of 1 ml/min and the protein was eluted in 1.5 CV. Peak fractions (1.5 ml each) were collected and screened by 12% or 4-20% Bis-Tris-SDS gel electrophoresis. Fractions containing the protein were pooled and a final concentration of 7.5 mM DTT was added in order to reduce the protein molecules. Following a 2 hour incubation at room temperature, the mixture was diluted 5× with water and subjected to dialysis into 4.5 L 3 mM $NaH_2PO_4$, 7 mM $Na_2HPO_4$, 2 mM KCl, 120 mM NaCl. Dialysis was continued for 3-4 days with fresh buffer change at least 3 times. The dialyzed material was then filtered through an 0.2 μm filter and the pH was adjusted to 5 with acetic acid. The column was equilibrated with 10 CV of Buffer 1 (25 mM Ammonium Acetate pH5) followed by a 20 minute gradient to 100% buffer B (25 mM Ammonium Acetate pH5/1M NaCl) post injection. Peak fractions (0.5 ml each) were collected and screened by 12% or 4-20% Bis-Tris-SDS gel electrophoresis. Product containing fractions were pooled and diluted 2× into Buffer A (0.1% TFA/water). The protein was then chromatographed on C4 Reverse Phase-HPLC (Beckman system Gold), using a 5 ml loop and flow rate of 1 ml/min with the following program: 10% Buffer A for duration of injection, 10 minute gradient to 40% Buffer B (0.1% TFA/ACN), 30 minute gradient to 50% Buffer B, and 5 minute gradient to 100% Buffer B. Peak fractions (0.5 ml each) were collected and screened by 12% or 4-20% Bis-Tris-SDS gel electrophoresis. Protein containing fractions were dried down and resuspended in 0.1M MES pH 6.1 for analysis and assays.

EXAMPLE 3

Site-Specific Cysteine PEGylation and Purification

A protocol was established to PEGylate the cysteine containing IL4 RA muteins via a stable thioether linkage between the sulfhydryl of the protein and the maleimide group of a linear 22 kD methoxy-polyethylene glycol-maleimide derivative (Nektar Therapeutics). A 2-fold molar excess of mPEG-MAL 22 kD reagent was added to 60 μM of protein dissolved in reaction buffer, 0.1M MES, pH 6. After 0.5 hour at room temperature, the reaction was terminated with 2-fold molar excess of cysteine over mPEG-MAL 22 kD (FIG. 1). PEGylated protein was purified away from unreacted mPEG-MAL 22 kD (quenched with cysteine) and unreacted IL4 RA cysteine mutein by cation exchange and size exclusion chromatography. Crude reaction mixtures were applied to Vivapure Mini S cation exchange columns (Vivascience) equilibrated with 0.4 mL of 0.1M MES, pH 6. The columns were washed twice with 0.4 mL of 0.1M MES, pH 6 followed by centrifugation at 2,000×g after each wash. The samples were eluted by centrifugation from the column with 0.4 mL of 0.6M NaCl/0.1M MES, pH6. The 0.4 mL elutions were loaded onto a TSK-GEL G2000SWXL HPLC sizing column (Tosoh Biosep) using a Beckman HPLC system Gold. The samples were resolved using a Phosphate Buffered Saline (Dulbecco's PBS) mobile phase at a flow rate of 1 ml/min for 30 min. Peak fractions (0.5 ml) were collected and evaluated by 4-12% Bis-Tris-SDS gel electrophoresis for PEGylated protein. Fractions containing the product were pooled and concentrated using an Ultrafree Biomax-5 device (Millipore) per manufacturer's protocol to approximately 60 μM (or 1 mg/ml) for analysis and in vitro assays. Final concentrations for the PEGylated proteins were determined by amino acid analysis. Final yields are depicted in Table 5.

TABLE 5

Purification yields for PEGylated IL4RA cysteine muteins

| Mutein | PEGylated (mg, nitial) | PEGylated (mg, final) | % Recovery |
|---|---|---|---|
| IL4RA | ND | ND | ND |
| T28C | 0.267 | 0.064 | 24.0 |
| S36C | 0.392 | 0.057 | 14.5 |
| K37C | 0.264 | 0.011 | 4.2 |
| N38C | 0.387 | 0.083 | 21.4 |
| A104C | 0.213 | 0.010 | 4.7 |
| N105C | 0.289 | 0.044 | 15.2 |
| Q106C | 0.125 | 0.023 | 18.4 |
| Average | 0.176 | 0.042 | 14.6 |

EXAMPLE 4

BiaCore IL-4 Receptor Binding Assay

IL-4 receptor was immobilized on a BIAcore CM5 research grade sensor chip through amine coupling. The sensor surface was activated with an EDC/NHS pulse. IL-4 receptor was dissolved in 10 mM acetate buffer (pH 5.0) and injected into flowcell 2 followed by a pulse of 1.0M ethanolamine-HCL to deactivate the surface. The immobilization level for the receptor was ~300 RU. Flowcell 1 was also activated without a ligand to function as a blank. The Biacore Wizard was used to perform kinetics analysis. Candidate IL4RE antagonists were diluted in HBS-EP (running buffer) and injected at 30 ul/minute flow rate for 3 minutes and a dissociation time of 15 minutes. Regeneration of the chip was performed by two 30 second injections of 10 mM Glycine pH2.5 (flow 100 ul/min) to baseline prior to next injection in the concentration series. Dissociation constant ($K_D$) values were calculated for each candidate based on direct binding kinetics (Table 5). Results show constructs IL4-RE-A104C, IL4-RE-$N_{105}$C, and IL4-RE-Q106C all yielded dissociation constants below 0.6 nM.

EXAMPLE 5

TF-1 Cell Proliferation Assay

The proliferative response of TF-1 cells to IL-4 (0.5 ng/ml, 0.033 nM) or IL-13 (5 ng/ml, 0.416 nM), was used to assess the functional antagonistic activity of IL-4RE molecules. In this assay, TF-1 cells were cultured for 2-4 days in 96 well plates ($1\times10^4$/well, 100 μl volume) in RPMI+10% serum with or without IL-4 or IL-13 and IL-4RE molecules. GM-CSF treatment was used as a positive control. Twenty-four hours before the final reading, 10 μl AlamarBlue (10% vol) was added to each well. Fluorescence was determined at 530/590 nm using a WALLAC Victor 2. Inhibitory Concentration 50% ($IC_{50}$) was calculated based on dose titration of the candidate IL-4RE molecules. A summary of the TF-1 bioassay results for IL-4 and IL-13 inhibition are shown in Table 6. Results indicate that constructs IL4-RE-K37C, IL4-RE-N38C and IL4-RE-A104C demonstrated comparable $IC_{50}$ values to that of IL-4-RA in the presence of IL-4 or IL-13.

TABLE 6

PEG-IL4RE BIAcore binding assay and bioactivity evaluation of PEGylated muteins versus IL4RA in TF-1 cell proliferation assays.

| Mutein | BIAcore Affinity, nM | TF-1/IL-4 $IC_{50}$, nM | TF-1/IL-13 $IC_{50}$, nM |
|---|---|---|---|
| BAY 16-9996 IL-4RA | 0.11 | 0.56 + 0.86 (n = 17) | 1.17 + 1.77 (n = 6) |
| IL4-RE-T28C | 0.89 | 2.35 + 0.75 (n = 2) | 2.87 + 0 (n = 1) |
| IL4-RE-S36C | 1.15 | 1.20 + 0.02 (n = 2) | 1.21 + 0(n = 1) |
| IL4-RE-K37C | 0.74 | 0.82 + 0.01 (n = 2) | 1.22 + 0.58 (n = 2) |
| IL4-RE-N38C | 0.77 | 0.70 + 0.18 (n = 2) | 1.24 + 0.58 (n = 2) |
| IL4-RE-A104C | 0.56 | 0.55 + 0.10 (n = 2) | 1.34 + 1.21 (n = 2) |
| IL4-RE-N105C | 0.59 | 2.26 + 0.20 (n = 2) | 2.11 + 0(n = 1) |
| IL4-RE-Q106C | 0.52 | 2.44 + 0.68 (n = 2) | 1.95 + 0(n = 1) |

EXAMPLE 6

Primary Cell Proliferation Assay

The proliferative response of human primary cells (T- and B-cells) to IL-4 was also evaluated following IL-4RE molecule pre-treatment. Peripheral blood mononuclear cells (PBMCs) were isolated from peripheral blood and some were treated with PHA for 4 days to induce T cell blast formation. PBMCs were also treated with anti-CD40 to activate B cell activity and used immediately. The cells were seeded in 96-well plates ($10^5$ cells per well). PHA T-cell blasts and B cells preparations were stimulated for 3 days with IL-4 (10 ng/ml, 0.667 nM) in the presence of varying concentrations of IL-4RE molecules. The incorporation of tritiated thymidine in the last 20 hours of incubation was used as an indicator of proliferation. The results of these assays are shown in Table 7. Results indicate that all PEGylated constructs demonstrated an $IC_{50}$ less than 5-fold greater than that of IL-4RA for both primary cell assays.

TABLE 7

PEG-IL4RE bioactivity evaluation in B-cell and T-cell blast proliferation assays.

| Mutein | B-cell $IC_{50}$, nM | T-cell blast $IC_{50}$, nM |
|---|---|---|
| BAY 16-9996 IL-4RA | 0.86 + 0.42 (n = 10) | 3.22 + 3.26 (n = 16) |
| IL4-RE-K37C | 3.73 + 2.15 (n = 2) | 13.86 + 12.77 (n = 2) |
| IL4-RE-N38C | 3.33 + 2.68 (n = 2) | 9.94 + 8.99 (n = 2) |
| IL4-RE-A104C | 3.29 + 1.46 (n = 2) | 4.67 + 4.65 (n = 2) |

EXAMPLE 7

Rat Pharmacokinetics Studies

Adult male Sprague-Dawley rats weighing 250 to 300 grams were used. The rats were cannulated with jugular vein catheter for blood sample collection. In addition, the rats of intravenous (IV) dose group were cannulated with femoral vein catheters for drug administration.

The rats were given either IL-4RA or a modified IL-4 mutein receptor antagonist at doses of 1 and 0.5 mg/kg, respectively. Both IV and SC (subcutaneous) routes of administration were used. The IV dose was given by injection directly into the indwelling femoral vein catheter. The SC dose was given by injection into the dorsal thoracic region. Three rats were used for each dose group.

Following a single bolus injection (IV or SC), blood samples were collected at predose and at predetermined times up to 168 hours post dose. Centrifugation for samples began within 1 hour of collection. Plasma was harvested and placed on dry ice prior to storage at approximately −70° C.

Plasma concentrations of IL-4RA and modified mutein were quantified with an enzyme-linked immunoassay. Anti-IL-4 antibody was used as coating and detection reagents. The lower limit of quantification for this assay was 0.2 ng/ml. Pharmacokinetic parameters were derived by non-compartmental analysis using WinNonlin (Pharsight, Mountain view, Calif.). Of particular interest is the assessment of absorption and elimination kinetics, distribution volumes as well as the amount absorbed.

EXAMPLE 8

*E. coli*-Encoded IL-4 Mutein

High purity and high yield inclusion body expression directly affects manufacturing ability and costs. It has been shown that IL-4 triple mutein molecules can be made in the laboratory by including an IL-4 triple mutein construct utilizing human DNA codons into an appropriate plasmid vector suitable for expression in *E. coli*. Although small quantities of inclusion bodies can be obtained from an IL-4 triple mutein construct using human codons, the *E. coli* fermentation process is not robust. It was observed that expression of an IL-4 triple mutein construct using human codons can be toxic to *E. coli* cells causing lysis, resulting in low yields of inclusion bodies. Without being limited to certain theories, this observation is likely due to limited quantities of human codons in *E. coli*. In order to improve the process, the *E. coli*-codon IL-4RA plasmid was used to make *E. coli*-encoded IL4-RE-T13D with QuickChange (Strategene). Briefly, IL-4RA plasmid was altered by QuickChange and suitable primers to alter the codons at either position alanine 104 (codon GCT) or asparagine 38 (codon AAC) to a cysteine (codon TGC). Two *E. coli*-codon IL4-RE-T13D plasmids were made that coded for IL-4™ (IL4-RE-T13D) molecules (Table 8).

TABLE 8

*E. coli*-codon IL-4TM Plasmids

| SEQ ID NO | Name | Sequence |
|---|---|---|
| 34 | *E. coli*-codon 104C sequence | atgcacaaatgcgatatcaccctgcaggaaatca tcaaaaccctgaattctctgaccgaacagaaaac cctgtgcaccgaactgaccgttaccgacatcttc |

TABLE 8-continued

*E. coli*-codon IL-4TM Plasmids

| SEQ ID NO | Name | Sequence |
|---|---|---|
| | | gctgcttcgaaaaacaccaccgaaaaagaaacct<br>tctgccgtgctgctaccgttctgcgtcagttcta<br>ctctcaccacgaaaaagacacccgttgcctgggt<br>gctaccgctcagcagttccaccgtcacaaacagc<br>tgatccgtttcctgaaacgtctggaccgtaacct<br>gtggggtctggctggtctgaacagctgcccggtt<br>aaagaatgcaaccagtctaccctggaaaacttcc<br>tggaacgtctgaaaaccatcatggacgaaaaaga<br>ctctaaatgctcttcttaataa |
| 35 | *E. coli*-codon 38C sequence | atgcacaaatgcgatatcaccctgcaggaaatca<br>tcaaaaccctgaattctctgaccgaacagaaaac<br>cctgtgcaccgaactgaccgttaccgacatcttc<br>gctgcttcgaaatgcaccaccgaaaaagaaacct<br>tctgccgtgctgctaccgttctgcgtcagttcta<br>ctctcaccacgaaaaagacacccgttgcctgggt<br>gctaccgctcagcagttccaccgtcacaaacagc<br>tgatccgtttcctgaaacgtctggaccgtaacct<br>gtggggtctggctggtctgaacagctgcccggtt<br>aaagaagctaaccagtctaccctggaaaacttcc<br>tggaacgtctgaaaaccatcatggacgaaaaaga<br>ctctaaatgctcttcttaataa |
| 36 | *E. coli*-codon T13D N38C sequence | atgcacaaatgcgatatcaccctgcaggaaatca<br>tcaaagacctgaattctctgaccgaacagaaaac<br>cctgtgcaccgaactgaccgttaccgacatcttc<br>gctgcttcgaaatgcaccaccgaaaaagaaacct<br>tctgccgtgctgctaccgttctgcgtcagttcta<br>ctctcaccacgaaaaagacacccgttgcctgggt<br>gctaccgctcagcagttccaccgtcacaaacagc<br>tgatccgtttcctgaaacgtctggaccgtaacct<br>gtggggtctggctggtctgaacagctgcccggtt<br>aaagaagctaaccagtctaccctggaaaacttcc<br>tggaacgtctgaaaaccatcatggacgaaaaaga<br>ctctaaatgctcttct |
| 37 | *E. coli* plasmid with *E. coli*-codon T13D N38C sequence | aaatgctcttcttaataaggatccggctgctaac<br>aaagcccgaaaggaagctgagttggctgctgcca<br>ccgctgagcaataactagcataaccccttggggc<br>ctctaaacgggtcttgaggggttttttgctgaaa<br>ggaggaactatatccggataattcttagaaaaac<br>tcatcgagcatcaaatgaaactgcaatttattca<br>tatcaggattatcaataccatatttttgaaaaag<br>ccgtttctgtaatgaaggagaaaactcaccgagg<br>cagttccataggatggcaagatcctggtatcggt<br>ctgcganccgactcgtccaacatcaatacaacct<br>attaatttcccctcgtcaaaaataaggnatcaag<br>tgagaaatcaccatgagtgacgactgaatccggt<br>gagaatggcaaaagcttatgcatttctttccaga<br>cttgttcaacaggccagccattacgctcgtcatc<br>aaaatcactcgcatcaaccaaaccgttattcatt<br>cgtgattgcgcctgagcgagacgaaatacgcgat<br>cgctgttaaaaggacaattacaaacaggaatcga<br>atgcaaccggcgcaggaacactgccagcgcatca<br>acaatattttcacctgaatcaggatattcttcta<br>atacctggaatgctgttttcccggggatcgcagt<br>ggtgagtaaccatgcatcatcaggagtacggata<br>aaatgcttgatggtcggaagaggcataaattccg<br>tcagccagtttagtctgaccatctcatctgtaac<br>atcattggcaacgctacctttgccatgtttcaga<br>aacaactctggcgcatcgggcttcccatacaatc<br>gatagattgtcgcacctgattgcccgacattatc<br>gcgagcccatttatacccatataaatcagcatcc<br>atgttggaatttaatcgcggcctcgagcaagacg<br>tttcccgttgaatatggctcataacaccccttgt<br>attactgtttatgtaagcagacagttttattgtt<br>catgaccaaaatcccttaacgtgagttttcgttc<br>cactgagcgtcagaccccgtagaaaagatcaaag<br>gatcttcttgagatcctttttttctgcgcgtaat<br>ctgctgcttgcaaacaaaaaaaccaccgctacca<br>gcggtggtttgtttgccggatcaagagctaccaa<br>ctctttttccgaaggtaactggcttcagcagagc<br>gcagataccaaatactgtccttctagtgtagccg |

TABLE 8-continued

*E. coli*-codon IL-4TM Plasmids

| SEQ ID NO | Name | Sequence |
|---|---|---|
| | | tagttaggccaccacttcaagaactctgtagcac<br>cgcctacatacctcgctctgctaatcctgttacc<br>agtggctgctgccagtggcgataagtcgtgtctt<br>accgggttggactcaagacgatagttaccggata<br>aggcgcagcggtcgggctgaacggggggttcgtg<br>cacacagcccagcttggagcgaacgacctacacc<br>gaactgagatacctacagcgtgagctatgagaaa<br>gcgccacgcttcccgaagggagaaaggcggacag<br>gtatccggtaagcggcagggtcggaacaggagag<br>cgcacgagggagcttccagggggaaacgcctggt<br>atctttatagtcctgtcgggtttcgccacctctg<br>acttgagcgtcgatttttgtgatgctcgtcaggg<br>gggcggagcctatggaaaaacgccagcaacgcgg<br>cctttttacggttcctggccttttgctggccttt<br>tgctcacatgttctttcctgcgttatcccctgat<br>tctgtggataaccgtattaccgcctttgagtgag<br>ctgataccgctcgccgcagccgaacgaccgagcg<br>cagcgagtcagtgagcgaggaagcggaagagcgc<br>ctgatgcggtattttctccttacgcatctgtgcg<br>gtatttcacaccgcaatggtgcactctcagtaca<br>atctgctctgatgccgcatagttaagccagtata<br>cactccgctatcgctacgtgactgggtcatggct<br>gcgccccgacacccgccaacacccgctgacgcgc<br>cctgacgggcttgtctgctcccggcatccgctta<br>cagacaagctgtgaccgtctccgggagctgcatg<br>tgtcagaggttttcaccgtcatcaccgaaacgcg<br>cgaggcagctgcggtaaagctcatcagcgtggtc<br>gtgaagcgattcacagatgtctgcctgttcatcc<br>gcgtccagctcgttgagtttctccagaagcgtta<br>atgtctggcttctgataaagcgggccatgttaag<br>ggcggtttttttcctgtttggtcactgatgcctcc<br>gtgtaagggggatttctgttcatgggggtaatga<br>taccgatgaaacgagagaggatgctcacgatacg<br>ggttactgatgatgaacatgcccggttactggaa<br>cgttgtgagggtaaacaactggcggtatggatgc<br>ggcgggaccagagaaaaatcactcagggtcaatg<br>ccagcgctcatgagcccgaagtggcgagcccgat<br>cttccccatcggtgatgtcggcgatataggcgcc<br>agcaaccgcacctgtggcgccggtgatgccggcc<br>acgatgcgtccggcgtagaggatcgagatccatt<br>tacgttgacaccatcgaatggtgcaaaacctttc<br>gcggtatggcatgatagcgcccggaagagagtca<br>attcagggtggtgaatgtgaaaccagtaacgtta<br>tacgatgtcgcagagtatgccggtgtctcttatc<br>agaccgtttcccgcgtggtgaaccaggccagcca<br>cgtttctgcgaaaacgcgggaaaaagtggaagcg<br>gcgatggcggagctgaattacattcccaaccgcg<br>tggcacaacaactggcgggcaaacagtcgttgct<br>gattggcgttgccacctccagtctggccctgcac<br>gcgccgtcgcaaattgtcgcggcgattaaatctc<br>gcgccgatcaactgggtgccagcgtggtggtgtc<br>gatggtagaacgaagcggcgtcgaagcctgtaaa<br>gcggcggtgcacaatcttctcgcgcaacgcgtca<br>gtgggctgatcattaactatccgctggatgacca<br>ggatgccattgctgtggaagctgcctgcactaat<br>gttccggcgttatttcttgatgtctctgaccaga<br>cacccatcaacagtattattttctcccatgaaga<br>cggtacgcgactgggcgtggagcatctggtcgca<br>ttgggtcaccagcaaatcgcgctgttagcgggcc<br>cattaagttctgtctcggcgcgtctgcgtctggc<br>tggctggcataaatatctcactcgcaatcaaatt<br>cagccgatagcggaacgggaaggcgactggagtg<br>ccatgtccggttttcaacaaaccatgcaaatgct<br>gaatgagggcatcgttcccactgcgatgctggtt<br>gccaacgatcagatggcgctgggcgcaatgcgcg<br>ccattaccgagtccgggctgcgcgttggtgcgga<br>tatctcggtagtgggatacgacgataccgaagac<br>agctcatgttatatcccgccgttaaccaccatca<br>aacaggattttcgcctgctggggcaaaccagcgt<br>ggaccgcttgctgcaactctctcagggccaggcg<br>gtgaagggcaatcagctgttgcccgtctcactgg<br>tgaaaagaaaaaccaccctggctcgagaaatcat<br>aaaaaatttatttgctttgtgagcggataacaat |

TABLE 8-continued

*E. coli*-codon IL-4TM Plasmids

| SEQ ID NO | Name | Sequence |
|---|---|---|
| | | tataatagattcaattgtgagcggataacaattt cacacatctagaaataattttatttaactttaag aaggagatatacatatgcacaaatgcgatatcac cctgcaggaaatcatcaaagacctgaattctctg accgaacagaaaaccctgtgcaccgaactgaccg ttaccgacatcttcgctgcttcgaaatgcaccac cgaaaaagaaaccttctgccgtgctgctaccgtt ctgcgtcagttctactctcaccacgaaaaagaca cccgttgcctgggtgctaccgctcagcagttcca ccgtcacaaacagctgatccgtttcctgaaacgt ctggaccgtaacctgtggggtctggctggtctga acagctgcccggttaaagaagctaaccagtctac cctggaaaacttcctggaacgtctgaaaaccatc atggacgaaaaagactctaaatgctcttcttaat aaggatccggctgctaacaaagcccgaaaggaag ctgag |

EXAMPLE 9

PEGylated IL-4/IL-13 Inhibitor

Figure 2:
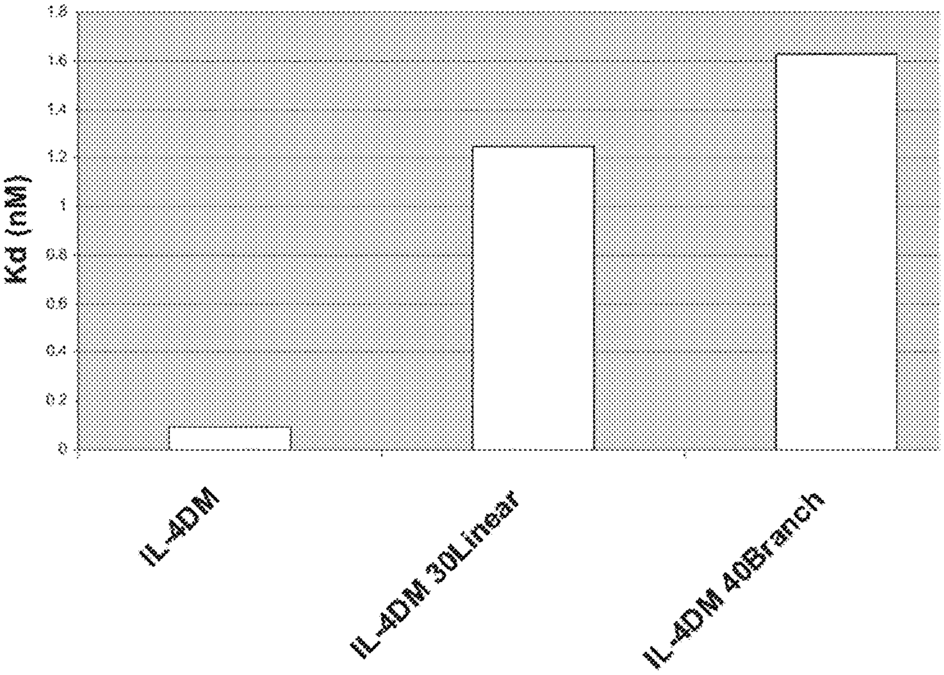
FIG. 2 is a graphical diagram showing data from BIAcore binding to IL-4Rα comparing the IL-4 double mutein (IL-4DM) to the same molecule with a 30 kD linear or a 40 kD branched PEG at position 38C.

When IL-4™-N38C or IL-4™-A104C is PEGylated with a maleimide-PEG (20 kDa linear from Nektar, Dow or NOF; 30 kDa linear from Nektar, Dow or NOF; 40 kDa linear from Nektar, Dow or NOF; or a 40 kDa branched from Nectar or NOF), the activity decreases significantly when assayed using the BIAcore method, TF-1 cell-based assay or primary B or T lymphocytes from peripheral blood (FIG. 2).

Additionally, it was observed that the position in which the additional cysteine is placed is important. As shown in Table 9, PEGylated 104C looses about 2-fold activity more than PEGylated 38C in the TF-1 activity assay.

TABLE 10

Comparison of activities of IL-4DM to PEGylated IL-4TM

| | Molecule | | | | | | | | | | | |
|---|---|---|---|---|---|---|---|---|---|---|---|---|
| | IL-4DM | | | | N38C-40B | | | | 104C-40B | | | |
| | Cytokine assay | | | | | | | | | | | |
| | IL-4 | | IL-13 | | IL-4 | | IL-13 | | IL-4 | | IL-13 | |
| EC50 average | 0.386 | | 2.23 | | 2.08 | | 11 | | 2.49 | | 12.1 | |
| EC50 std dev | 0.275 | n = 18 | 1.08 | n = 18 | 1.32 | n = 11 | 7.39 | n = 11 | 0.73 | n = 5 | 4.55 | n = 6 |
| >95% inhibition ave | 24.6 | | 154 | | 140 | | 529 | | 360 | | 1060 | |
| >95% inhibition std | 14.4 | n = 7 | 106 | n = 14 | 89.6 | n = 7 | 272 | n = 7 | 22.4 | n = 5 | 545 | n = 5 |

Figure 3:
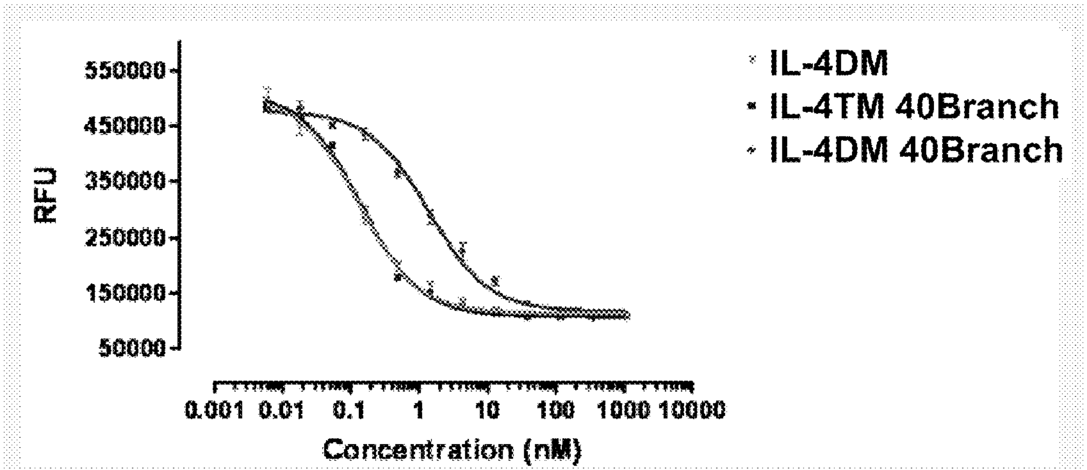
FIG. 3 is a graphical diagram showing data from inhibition of TF-1 growth with IL-4 stimulation revealing that PEGylated IL-4™ (T13D/R121D/Y124D) is more potent than PEGylated IL-4DM and is equally potent to IL-4DM (R121D/Y124D).

To compensate for this loss of activity an additional T13D mutation was included onto the IL-4™-N38C using QuikChange, appropriate primers, and the *E. coli-codon* N38C plasmid. This T13D mutation has previously been shown to increase binding affinity to the IL-4Rα (see U.S. Pat. No. 6,028,176, incorporated herein by reference). As shown in FIG. 3, PEGylated T13D-N38C with 40 kDa branched PEG has equal BIAcore as the unPEGylated IL-4DM (R121D/Y124D), but the data cannot accurately predict the cell-based assay since PEGylation affects the on-rate of all PEGylated IL-4™ molecules. It is the off-rate that is generally potency-determining in a bioassay. Using the TF-1 cell-based assay, PEGylated T13D-N38C with 40 kDa branched PEG has equal activity as IL-4DM.

Similar results were observed in a primary T cell assay. In this assay whole blood from 10 donors was collected and PBMCs isolated. PBMCs were incubated for 4 days with PHA-P, and these "blasts" were then used for the assay. Blasts were incubated for 3 days with IL-4 plus one of 12 dilutions of IL-4™ test compound. In the last 18 hours, 3H-thymidine was added to the culture. Cells were harvested and DNA that incorporated 3H-thymidine was quantified on a b-counter. Table 10 demonstrates the loss of potency with PEGylation and the improvement in potency gained from PEGylating at 38C compared to 104C.

TABLE 10

| Candidate | $IC_{50}$ (nM) | >95% Inhibition (nM) | Fold increase in IC50 (relative to IL-4DM) |
|---|---|---|---|
| 104C 40B | 8.0 ± 2.07 | ~171.4 | 7.4 |
| 104C 30L | 4.93 ± 0.79 | ~135.7 | 4.6 |
| 38C 40B | 2.43 ± 0.5 | ~55.7 | 2.3 |
| T13D 40B | 3.28 ± 1.428 | ~38.6 | 3.1 |
| T13D | 0.714 ± 0.214 | ~10.7 | 0.67 |
| IL4-DM | 1.071 ± 0.714 | ~22.1 | 1 |

Studies were also done in primary B cells. Similarly, whole blood from 5 donors was collected and PBMCs isolated. PBMCs were incubated for 3 days with mouse anti-human CD40, IL-4, and one of 12 dilutions of IL-4™ test compound. In the last 18 hours, 3H-thymidine was added to the culture. Cells were harvested and DNA that incorporated 3H-thymidine was quantified on a b-counter (Table 11).

TABLE 11

| Candidate | IC50 (nM) | >95% Inhibition (nM) | Fold increase in IC50 (relative to IL-4DM) |
|---|---|---|---|
| 104C 40B | 19.42 ± 6.28 | ~335.6 | 11.3 |
| 104C 30L | 13.0 ± 5.21 | ~142.8 | 7.6 |
| 38C 40B | 6.85 ± 2.21 | ~96.4 | 4.0 |
| T13D 40B | 2.43 ± 1.07 | ~22.1 | 1.4 |
| T13D | 0.5 ± 0.143 | ~7.14 | 0.3 |
| IL-4DM | 1.71 ± 0.64 | ~25.7 | 1 |

Again the improvement of PEGylation at the 38C position compared to the 104C position was observed as well as the increased or similar potency of the T13D and the T13D 40B constructs, respectively, compared to IL-4DM (R121D/Y124D).

EXAMPLE 10

Improving the Refolding Yields of an IL-4/IL-13 Inhibitor

IL-4™ (T13D/R121D/Y124D) contains a $7^{th}$ cysteine residue in the protein sequence at either position 38C or 104C. This odd cysteine reduces the efficiently of refolding IL-4™ from inclusion bodies. The addition of glutathione to the IL-4™ refold buffer optimizing the yield of IL-4™ refolding while still preserving the ability of 38C or 104C to be PEGylated by a maleimide-linked PEG molecule. In addition to adding glutathione to the refolding mixture, there is a time-dependency of refolding to optimize the yields of IL-4™ for PEGylation. Maximized protein refolding yields are monitored by the BIAcore assay. Once the maximum refolding yield is achieved, the pH of the refold solution is lowered with an acid to a pH where cysteine oxidation chemistries are no longer efficient. Low pH is maintained until IL-4™ is reacted with maleimide-PEG at a more neutral pH where the cysteine-maleimide bond forms.

REFERENCES

1. Ying, S., M. Humbert, J. Barkans, C. J. Corrigan, R. Pfister, G. Menz, M. Larche, D. S. Robinson, S. R. Durham and A. B. Kay. 1997. Expression of IL-4 and IL-5 mRNA and protein product by CD4+ and CD8+ T cells, eosinophils, and mast cells in bronchial biopsies obtained from atopic and nonatopic (intrinsic) asthmatics. *J. Immunol.* 158: 3539-3544.
2. Huang, S. K., H. Q. Xiao, J. Kleine-Tebbe, G. Paciotti, D. G. Marsh, L. M. Lichtenstein and M. C. Liu. 1995. IL-13 expression at the sites of allergen challenge in patients with asthma. *J. Immunol.* 155: 2688-2694.
3. Zhu, Z., R J. Homer, Z. Wang, Q. Chen, G. P. Geba, J. Wang, Y. Zhang and J. A. Elias. 1999. Pulmonary expression of interleukin-13 causes inflammation, mucus hypersecretion, subepithelial fibrosis, physiologic abnormalities, and eotaxin production. *J. Clin. Invest.* 103: 779-788.
4. Henderson, W. R. J., E. Y. Chi and C. R. Maliszewski. 2000. Soluble IL-4 receptor inhibits airway inflammation following allergen challenge in a mouse model of asthma. *J. Immunol.* 164:1086-1095.
5. Sambrook (1989) Current Protocols in Molecular Biology, John Wiley & Sons, New York, N.Y., 1995.

A Sequence Listing is attached electronically herewith and uploaded via the Electronic Filing System of the United States Patent and Trademark Office. The entire contents of the Sequence Listing are incorporated herein by reference. The file details appear as follows:

(a) "AERO1210_4SEQLIST.txt"—32 Kilobytes

The Sequence Listing, "AERO1210_4SEQLIST.txt," was created on Nov. 14, 2007 and was uploaded on Nov. 14, 2007.

Although the invention has been described with reference to the above example, it will be understood that modifications and variations are encompassed within the spirit and scope of the invention. Accordingly, the invention is limited only by the following claims.

What is claimed is:

1. A modified IL-4 mutein receptor antagonist coupled to a non-protein polymer at an amino acid residue at position 28, 36, 37, 38, 104, 105, or 106 of IL-4, wherein the amino acids at positions 13, 121 and 124 are aspartic acid, wherein the amino acids are numbered according to wild type human IL-4, and wherein the non-protein polymer is polyethylene glycol, polypropylene glycol or a polyoxyalkylene.

2. The modified IL-4 mutein receptor antagonist of claim 1, wherein the non-protein polymer is coupled at an amino acid residue at position 37, 38, or 104 of IL-4.

3. The modified IL-4 mutein receptor antagonist of claim 1, wherein the antagonist consists of the amino acid sequence as set forth in SEQ ID NO: 33.

4. The modified IL-4 mutein receptor antagonist of claim 1, wherein the non-protein polymer is polyethylene glycol.

5. The modified IL-4 mutein receptor antagonist of claim 4, wherein the polyethylene glycol is linear.

6. The modified IL-4 mutein receptor antagonist of claim 4, wherein the polyethylene glycol is branched.

7. The modified IL-4 mutein receptor antagonist of claim 6, wherein the polyethylene glycol is about 3 kD to 50 kD.

8. The modified IL-4 mutein receptor antagonist of claim 7, wherein the polyethylene glycol is 40 kD.

9. A pharmaceutical composition comprising:

a) the modified IL-4 mutein receptor antagonist of claim 1; and b) a pharmaceutically acceptable carrier.

10. A pharmaceutical composition comprising:

a) the modified IL-4 mutein receptor antagonist of claim 8; and b) a pharmaceutically acceptable carrier.

11. The modified IL-4 mutein receptor antagonist of claim 1, wherein the modified mutein receptor antagonist binds to the IL-4 receptor alpha chain with a $K_D$ of about 0.1 nM to about 10 μM, about 0.5 nM to about 1 μM, or about 1.0 nM to about 100 nM.

12. The modified IL-4 mutein receptor antagonist of claim 1, wherein the modified IL-4 mutein receptor antagonist inhibits the proliferative response of TF-1 cells to IL-4 with an $IC_{50}$ of about 0.1 nM to about 10 μM, about 0.5 nM to about 1 μM, or about 1.0 nM to about 100 nM.

13. The modified IL-4 mutein receptor antagonist of claim 1, wherein the modified IL-4 mutein receptor antagonist inhibits the proliferative response of TF-1 cells to IL-13 with an $IC_{50}$ of about 0.1 nM to about 10 μM, about 0.5 nM to about 1 μM, or about 1.0 nM to about 100 nM.

14. The modified IL-4 mutein receptor antagonist of claim 1, wherein the modified IL-4 mutein receptor antagonist inhibits the proliferative response of human B cells to IL-4 with an $IC_{50}$ of about 0.1 nM to about 10 μM, about 0.5 nM to about 1 μM, or about 1.0 nM to about 100 nM.

15. The modified IL-4 mutein receptor antagonist of claim 1, wherein the modified IL-4 mutein receptor antagonist inhibits the proliferative response of human T cells to IL-4 with an $IC_{50}$ of about 0.1 nM to about 10 μM, about 0.5 nM to about 1 μM, or about 1.0 nM to about 100 nM.

16. The modified IL-4 mutein receptor antagonist of claim 1, wherein the modified IL-4 mutein receptor antagonist has a plasma half-life which is at least about 2-10 fold greater than that of an unmodified IL-4 receptor antagonist.

17. The modified IL-4 mutein receptor antagonist of claim 1, wherein the modified IL-4 mutein receptor antagonist has a plasma half-life which is at least about 10-100 fold greater than that of an unmodified IL-4 receptor antagonist.

* * * * *

SEQUENCE LISTING

```
<160> NUMBER OF SEQ ID NOS: 37

<210> SEQ ID NO 1
<211> LENGTH: 396
<212> TYPE: DNA
<213> ORGANISM: Artificial sequence
<220> FEATURE:
<223> OTHER INFORMATION: Modified human sequence

<400> SEQUENCE: 1

atgcacaagt gcgatatcac cttacaggag atcatcaaaa ctttgaacag cctcacagag     60

cagaagactc tgtgcaccga gttgaccgta acagacatct ttgctgcctc caagaacaca    120

actgagaagg aaaccttctg cagggctgcg actgtgctcc ggcagttcta cagccaccat    180

gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aagccaacca gagtacgttg gaaaacttct tggaaaggct aaagacgatc    360

atggacgaga aagactcaaa gtgttcgagc taataa                              396


<210> SEQ ID NO 2
<211> LENGTH: 396
<212> TYPE: DNA
<213> ORGANISM: Artificial sequence
<220> FEATURE:
<223> OTHER INFORMATION: Modified human sequence

<400> SEQUENCE: 2
```

-continued

```
atgcacaagt gcgatatcac cttacaggag atcatcaaaa ctttgaacag cctcacagag     60

cagaagactc tgtgcaccga gttgtgcgta acagacatct ttgctgcctc caagaacaca    120

actgagaagg aaaccttctg cagggctgcg actgtgctcc ggcagttcta cagccaccat    180

gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aagccaacca gagtacgttg gaaaacttct tggaaaggct aaagacgatc    360

atggacgaga aagactcaaa gtgttcgagc taataa                              396
```

```
<210> SEQ ID NO 3
<211> LENGTH: 396
<212> TYPE: DNA
<213> ORGANISM: Artificial sequence
<220> FEATURE:
<223> OTHER INFORMATION: Modified human sequence

<400> SEQUENCE: 3

atgcacaagt gcgatatcac cttacaggag atcatcaaaa ctttgaacag cctcacagag     60

cagaagactc tgtgcaccga gttgaccgta acagacatct ttgctgcctg caagaacaca    120

actgagaagg aaaccttctg cagggctgcg actgtgctcc ggcagttcta cagccaccat    180

gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aagccaacca gagtacgttg gaaaacttct tggaaaggct aaagacgatc    360

atggacgaga aagactcaaa gtgttcgagc taataa                              396
```

```
<210> SEQ ID NO 4
<211> LENGTH: 396
<212> TYPE: DNA
<213> ORGANISM: Artificial sequence
<220> FEATURE:
<223> OTHER INFORMATION: Modified human sequence

<400> SEQUENCE: 4

atgcacaagt gcgatatcac cttacaggag atcatcaaaa ctttgaacag cctcacagag     60

cagaagactc tgtgcaccga gttgaccgta acagacatct ttgctgcctc ctgcaacaca    120

actgagaagg aaaccttctg cagggctgcg actgtgctcc ggcagttcta cagccaccat    180

gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aagccaacca gagtacgttg gaaaacttct tggaaaggct aaagacgatc    360

atggacgaga aagactcaaa gtgttcgagc taataa                              396
```

```
<210> SEQ ID NO 5
<211> LENGTH: 396
<212> TYPE: DNA
<213> ORGANISM: Artificial sequence
<220> FEATURE:
<223> OTHER INFORMATION: Modified human sequence

<400> SEQUENCE: 5

atgcacaagt gcgatatcac cttacaggag atcatcaaaa ctttgaacag cctcacagag     60

cagaagactc tgtgcaccga gttgaccgta acagacatct ttgctgcctc caagtgcaca    120

actgagaagg aaaccttctg cagggctgcg actgtgctcc ggcagttcta cagccaccat    180
```

-continued

```
gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aagccaacca gagtacgttg gaaaacttct tggaaaggct aaagacgatc    360

atggacgaga aagactcaaa gtgttcgagc taataa                              396


<210> SEQ ID NO 6
<211> LENGTH: 396
<212> TYPE: DNA
<213> ORGANISM: Artificial sequence
<220> FEATURE:
<223> OTHER INFORMATION: Modified human sequence

<400> SEQUENCE: 6

atgcacaagt gcgatatcac cttacaggag atcatcaaaa ctttgaacag cctcacagag     60

cagaagactc tgtgcaccga gttgaccgta acagacatct ttgctgcctc caagaacaca    120

actgagaagg aaaccttctg cagggctgcg actgtgctcc ggcagttcta cagccaccat    180

gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aatgcaacca gagtacgttg gaaaacttct tggaaaggct aaagacgatc    360

atggacgaga aagactcaaa gtgttcgagc taataa                              396


<210> SEQ ID NO 7
<211> LENGTH: 396
<212> TYPE: DNA
<213> ORGANISM: Artificial sequence
<220> FEATURE:
<223> OTHER INFORMATION: Modified human sequence

<400> SEQUENCE: 7

atgcacaagt gcgatatcac cttacaggag atcatcaaaa ctttgaacag cctcacagag     60

cagaagactc tgtgcaccga gttgaccgta acagacatct ttgctgcctc caagaacaca    120

actgagaagg aaaccttctg cagggctgcg actgtgctcc ggcagttcta cagccaccat    180

gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aagcctgcca gagtacgttg gaaaacttct tggaaaggct aaagacgatc    360

atggacgaga aagactcaaa gtgttcgagc taataa                              396


<210> SEQ ID NO 8
<211> LENGTH: 396
<212> TYPE: DNA
<213> ORGANISM: Artificial sequence
<220> FEATURE:
<223> OTHER INFORMATION: Modified human sequence

<400> SEQUENCE: 8

atgcacaagt gcgatatcac cttacaggag atcatcaaaa ctttgaacag cctcacagag     60

cagaagactc tgtgcaccga gttgaccgta acagacatct ttgctgcctc caagaacaca    120

actgagaagg aaaccttctg cagggctgcg actgtgctcc ggcagttcta cagccaccat    180

gagaaggaca ctcgctgcct gggtgcgact gcacagcagt tccacaggca caagcagctg    240

atccgattcc tgaaacggct cgacaggaac ctctggggcc tggcgggctt gaattcctgt    300

cctgtgaagg aagccaactg cagtacgttg gaaaacttct tggaaaggct aaagacgatc    360

atggacgaga aagactcaaa gtgttcgagc taataa                              396
```

-continued

<210> SEQ ID NO 9
<211> LENGTH: 130
<212> TYPE: PRT
<213> ORGANISM: Artificial sequence
<220> FEATURE:
<223> OTHER INFORMATION: Modified human sequence

<400> SEQUENCE: 9

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130
```

<210> SEQ ID NO 10
<211> LENGTH: 130
<212> TYPE: PRT
<213> ORGANISM: Artificial sequence
<220> FEATURE:
<223> OTHER INFORMATION: Modified human sequence

<400> SEQUENCE: 10

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Cys Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130
```

<210> SEQ ID NO 11
<211> LENGTH: 130
<212> TYPE: PRT

-continued

<213> ORGANISM: Artificial sequence
<220> FEATURE:
<223> OTHER INFORMATION: Modified human sequence

<400> SEQUENCE: 11

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Cys Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130
```

<210> SEQ ID NO 12
<211> LENGTH: 130
<212> TYPE: PRT
<213> ORGANISM: Artificial sequence
<220> FEATURE:
<223> OTHER INFORMATION: Modified human sequence

<400> SEQUENCE: 12

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Cys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130
```

<210> SEQ ID NO 13
<211> LENGTH: 130
<212> TYPE: PRT
<213> ORGANISM: Artificial sequence
<220> FEATURE:
<223> OTHER INFORMATION: Modified human sequence

<400> SEQUENCE: 13

-continued

```
Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Cys Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130


<210> SEQ ID NO 14
<211> LENGTH: 130
<212> TYPE: PRT
<213> ORGANISM: Artificial sequence
<220> FEATURE:
<223> OTHER INFORMATION: Modified human sequence

<400> SEQUENCE: 14

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Cys Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130


<210> SEQ ID NO 15
<211> LENGTH: 130
<212> TYPE: PRT
<213> ORGANISM: Artificial sequence
<220> FEATURE:
<223> OTHER INFORMATION: Modified human sequence

<400> SEQUENCE: 15

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
```

-continued

```
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Cys Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130


<210> SEQ ID NO 16
<211> LENGTH: 130
<212> TYPE: PRT
<213> ORGANISM: Artificial sequence
<220> FEATURE:
<223> OTHER INFORMATION: Modified human sequence

<400> SEQUENCE: 16

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Cys Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130


<210> SEQ ID NO 17
<211> LENGTH: 42
<212> TYPE: DNA
<213> ORGANISM: Artificial sequence
<220> FEATURE:
<223> OTHER INFORMATION: Amplification primer

<400> SEQUENCE: 17

gaagactctg tgcaccgagt tgtgcgtaac agacatcttt gc                        42


<210> SEQ ID NO 18
<211> LENGTH: 42
<212> TYPE: DNA
<213> ORGANISM: Artificial sequence
<220> FEATURE:
<223> OTHER INFORMATION: Amplification primer
```

<400> SEQUENCE: 18
gcaaagatgt ctgttacgca caactcggtg cacagagtct tc 42

<210> SEQ ID NO 19
<211> LENGTH: 39
<212> TYPE: DNA
<213> ORGANISM: Artificial sequence
<220> FEATURE:
<223> OTHER INFORMATION: Amplification primer

<400> SEQUENCE: 19
gtaacagaca tctttgctgc ctgcaagaac acaactgag 39

<210> SEQ ID NO 20
<211> LENGTH: 39
<212> TYPE: DNA
<213> ORGANISM: Artificial sequence
<220> FEATURE:
<223> OTHER INFORMATION: Amplification primer

<400> SEQUENCE: 20
ctcagttgtg ttcttgcagg cagcaaagat gtctgttac 39

<210> SEQ ID NO 21
<211> LENGTH: 45
<212> TYPE: DNA
<213> ORGANISM: Artificial sequence
<220> FEATURE:
<223> OTHER INFORMATION: Amplification primer

<400> SEQUENCE: 21
ccgtaacaga catctttgct gcctcctgca acacaactga gaagg 45

<210> SEQ ID NO 22
<211> LENGTH: 45
<212> TYPE: DNA
<213> ORGANISM: Artificial sequence
<220> FEATURE:
<223> OTHER INFORMATION: Amplification primer

<400> SEQUENCE: 22
ccttctcagt tgtgttgcag gaggcagcaa agatgtctgt tacgg 45

<210> SEQ ID NO 23
<211> LENGTH: 42
<212> TYPE: DNA
<213> ORGANISM: Artificial sequence
<220> FEATURE:
<223> OTHER INFORMATION: Amplification primer

<400> SEQUENCE: 23
gacatctttg ctgcctccaa gtgcacaact gagaaggaaa cc 42

<210> SEQ ID NO 24
<211> LENGTH: 42
<212> TYPE: DNA
<213> ORGANISM: Artificial sequence
<220> FEATURE:
<223> OTHER INFORMATION: Amplification primer

<400> SEQUENCE: 24
ggtttccttc tcagttgtgc acttggaggc agcaaagatg tc 42

<210> SEQ ID NO 25

-continued

<211> LENGTH: 41
<212> TYPE: DNA
<213> ORGANISM: Artificial sequence
<220> FEATURE:
<223> OTHER INFORMATION: Amplification primer

<400> SEQUENCE: 25
gaattcctgt cctgtgaagg aatgcaacca gagtacgttg g 41

<210> SEQ ID NO 26
<211> LENGTH: 41
<212> TYPE: DNA
<213> ORGANISM: Artificial sequence
<220> FEATURE:
<223> OTHER INFORMATION: Amplification primer

<400> SEQUENCE: 26
ccaacgtact ctggttgcat tccttcacag gacaggaatt c 41

<210> SEQ ID NO 27
<211> LENGTH: 39
<212> TYPE: DNA
<213> ORGANISM: Artificial sequence
<220> FEATURE:
<223> OTHER INFORMATION: Amplification primer

<400> SEQUENCE: 27
cctgtgaagg aagcctgcca gagtacgttg gaaaacttc 39

<210> SEQ ID NO 28
<211> LENGTH: 39
<212> TYPE: DNA
<213> ORGANISM: Artificial sequence
<220> FEATURE:
<223> OTHER INFORMATION: Amplification primer

<400> SEQUENCE: 28
gaagttttcc aacgtactct ggcaggcttc cttcacagg 39

<210> SEQ ID NO 29
<211> LENGTH: 44
<212> TYPE: DNA
<213> ORGANISM: Artificial sequence
<220> FEATURE:
<223> OTHER INFORMATION: Amplification primer

<400> SEQUENCE: 29
cctgtcctgt gaaggaagcc aactgcagta cgttggaaaa cttc 44

<210> SEQ ID NO 30
<211> LENGTH: 44
<212> TYPE: DNA
<213> ORGANISM: Artificial sequence
<220> FEATURE:
<223> OTHER INFORMATION: Amplification primer

<400> SEQUENCE: 30
gaagttttcc aacgtactgc agttggcttc cttcacagga cagg 44

<210> SEQ ID NO 31
<211> LENGTH: 390
<212> TYPE: DNA
<213> ORGANISM: Artificial sequence
<220> FEATURE:
<223> OTHER INFORMATION: Modified human sequence

<400> SEQUENCE: 31

-continued

```
atgcacaaat gcgatatcac cctgcaggaa atcatcaaag acctgaattc tctgaccgaa     60

cagaaaaccc tgtgcaccga actgaccgtt accgacatct tcgctgcttc gaaatgcacc    120

accgaaaaag aaaccttctg ccgtgctgct accgttctgc gtcagttcta ctctcaccac    180

gaaaaagaca cccgttgcct gggtgctacc gctcagcagt tccaccgtca caaacagctg    240

atccgtttcc tgaaacgtct ggaccgtaac ctgtggggtc tggctggtct gaacagctgc    300

ccggttaaag aagctaacca gtctaccctg gaaaacttcc tggaacgtct gaaaaccatc    360

atggacgaaa aagactctaa atgctcttct                                     390


<210> SEQ ID NO 32
<211> LENGTH: 130
<212> TYPE: PRT
<213> ORGANISM: Artificial sequence
<220> FEATURE:
<223> OTHER INFORMATION: Modified human sequence

<400> SEQUENCE: 32

Met His Lys Cys Asp Ile Thr Leu Gln Glu Ile Ile Lys Asp Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Asn Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130


<210> SEQ ID NO 33
<211> LENGTH: 130
<212> TYPE: PRT
<213> ORGANISM: Artificial sequence
<220> FEATURE:
<223> OTHER INFORMATION: Modified human sequence

<400> SEQUENCE: 33

Met His Lys Cys Asp Ile Thr Leu Gln Glu Ile Ile Lys Asp Leu Asn
1               5                   10                  15

Ser Leu Thr Glu Gln Lys Thr Leu Cys Thr Glu Leu Thr Val Thr Asp
            20                  25                  30

Ile Phe Ala Ala Ser Lys Cys Thr Thr Glu Lys Glu Thr Phe Cys Arg
        35                  40                  45

Ala Ala Thr Val Leu Arg Gln Phe Tyr Ser His His Glu Lys Asp Thr
    50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95
```

-continued

```
Leu Asn Ser Cys Pro Val Lys Glu Ala Asn Gln Ser Thr Leu Glu Asn
            100                 105                 110

Phe Leu Glu Arg Leu Lys Thr Ile Met Asp Glu Lys Asp Ser Lys Cys
        115                 120                 125

Ser Ser
    130


<210> SEQ ID NO 34
<211> LENGTH: 396
<212> TYPE: DNA
<213> ORGANISM: Artificial sequence
<220> FEATURE:
<223> OTHER INFORMATION: Modified E.coli sequence

<400> SEQUENCE: 34

atgcacaaat gcgatatcac cctgcaggaa atcatcaaaa ccctgaattc tctgaccgaa      60

cagaaaaccc tgtgcaccga actgaccgtt accgacatct tcgctgcttc gaaaaacacc     120

accgaaaaag aaaccttctg ccgtgctgct accgttctgc gtcagttcta ctctcaccac     180

gaaaaagaca cccgttgcct gggtgctacc gctcagcagt tccaccgtca caaacagctg     240

atccgtttcc tgaaacgtct ggaccgtaac ctgtggggtc tggctggtct gaacagctgc     300

ccggttaaag aatgcaacca gtctaccctg gaaaacttcc tggaacgtct gaaaaccatc     360

atggacgaaa aagactctaa atgctcttct taataa                               396


<210> SEQ ID NO 35
<211> LENGTH: 396
<212> TYPE: DNA
<213> ORGANISM: Artificial sequence
<220> FEATURE:
<223> OTHER INFORMATION: Modified E.coli sequence

<400> SEQUENCE: 35

atgcacaaat gcgatatcac cctgcaggaa atcatcaaaa ccctgaattc tctgaccgaa      60

cagaaaaccc tgtgcaccga actgaccgtt accgacatct tcgctgcttc gaaatgcacc     120

accgaaaaag aaaccttctg ccgtgctgct accgttctgc gtcagttcta ctctcaccac     180

gaaaaagaca cccgttgcct gggtgctacc gctcagcagt tccaccgtca caaacagctg     240

atccgtttcc tgaaacgtct ggaccgtaac ctgtggggtc tggctggtct gaacagctgc     300

ccggttaaag aagctaacca gtctaccctg gaaaacttcc tggaacgtct gaaaaccatc     360

atggacgaaa aagactctaa atgctcttct taataa                               396


<210> SEQ ID NO 36
<211> LENGTH: 390
<212> TYPE: DNA
<213> ORGANISM: Artificial sequence
<220> FEATURE:
<223> OTHER INFORMATION: Modified E.coli sequence

<400> SEQUENCE: 36

atgcacaaat gcgatatcac cctgcaggaa atcatcaaag acctgaattc tctgaccgaa      60

cagaaaaccc tgtgcaccga actgaccgtt accgacatct tcgctgcttc gaaatgcacc     120

accgaaaaag aaaccttctg ccgtgctgct accgttctgc gtcagttcta ctctcaccac     180

gaaaaagaca cccgttgcct gggtgctacc gctcagcagt tccaccgtca caaacagctg     240

atccgtttcc tgaaacgtct ggaccgtaac ctgtggggtc tggctggtct gaacagctgc     300

ccggttaaag aagctaacca gtctaccctg gaaaacttcc tggaacgtct gaaaaccatc     360
```

-continued atggacgaaa aagactctaa atgctcttct 390

<210> SEQ ID NO 37
<211> LENGTH: 4257
<212> TYPE: DNA
<213> ORGANISM: Artificial sequence
<220> FEATURE:
<223> OTHER INFORMATION: Modified E.coli sequence

<400> SEQUENCE: 37
aaatgctctt cttaataagg atccggctgc taacaaagcc cgaaaggaag ctgagttggc 60
tgctgccacc gctgagcaat aactagcata accccttggg gcctctaaac gggtcttgag 120
gggttttttg ctgaaaggag gaactatatc cggataattc ttagaaaaac tcatcgagca 180
tcaaatgaaa ctgcaattta ttcatatcag gattatcaat accatatttt tgaaaaagcc 240
gtttctgtaa tgaaggagaa aactcaccga ggcagttcca taggatggca agatcctggt 300
atcggtctgc gattccgact cgtccaacat caatacaacc tattaatttc ccctcgtcaa 360
aaataaggtt atcaagtgag aaatcaccat gagtgacgac tgaatccggt gagaatggca 420
aaagcttatg catttctttc cagacttgtt caacaggcca gccattacgc tcgtcatcaa 480
aatcactcgc atcaaccaaa ccgttattca ttcgtgattg cgcctgagcg agacgaaata 540
cgcgatcgct gttaaaagga caattacaaa caggaatcga atgcaaccgg cgcaggaaca 600
ctgccagcgc atcaacaata ttttcacctg aatcaggata ttcttctaat acctggaatg 660
ctgttttccc ggggatcgca gtggtgagta accatgcatc atcaggagta cggataaaat 720
gcttgatggt cggaagaggc ataaattccg tcagccagtt tagtctgacc atctcatctg 780
taacatcatt ggcaacgcta cctttgccat gtttcagaaa caactctggc gcatcgggct 840
tcccatacaa tcgatagatt gtcgcacctg attgcccgac attatcgcga gcccatttat 900
acccatataa atcagcatcc atgttggaat ttaatcgcgg cctcgagcaa gacgtttccc 960
gttgaatatg gctcataaca ccccttgtat tactgtttat gtaagcagac agttttattg 1020
ttcatgacca aaatccctta acgtgagttt tcgttccact gagcgtcaga ccccgtagaa 1080
aagatcaaag gatcttcttg agatcctttt tttctgcgcg taatctgctg cttgcaaaca 1140
aaaaaaccac cgctaccagc ggtggtttgt ttgccggatc aagagctacc aactcttttt 1200
ccgaaggtaa ctggcttcag cagagcgcag ataccaaata ctgtccttct agtgtagccg 1260
tagttaggcc accacttcaa gaactctgta gcaccgccta catacctcgc tctgctaatc 1320
ctgttaccag tggctgctgc cagtggcgat aagtcgtgtc ttaccgggtt ggactcaaga 1380
cgatagttac cggataaggc gcagcggtcg ggctgaacgg ggggttcgtg cacacagccc 1440
agcttggagc gaacgaccta caccgaactg agatacctac agcgtgagct atgagaaagc 1500
gccacgcttc ccgaagggag aaaggcggac aggtatccgg taagcggcag ggtcggaaca 1560
ggagagcgca cgagggagct tccaggggga aacgcctggt atctttatag tcctgtcggg 1620
tttcgccacc tctgacttga gcgtcgattt ttgtgatgct cgtcaggggg gcggagccta 1680
tggaaaaacg ccagcaacgc ggccttttta cggttcctgg ccttttgctg gccttttgct 1740
cacatgttct ttcctgcgtt atcccctgat tctgtggata accgtattac cgcctttgag 1800
tgagctgata ccgctcgccg cagccgaacg accgagcgca gcgagtcagt gagcgaggaa 1860
gcggaagagc gcctgatgcg gtattttctc cttacgcatc tgtgcggtat ttcacaccgc 1920
aatggtgcac tctcagtaca atctgctctg atgccgcata gttaagccag tatacactcc 1980

-continued

```
gctatcgcta cgtgactggg tcatggctgc gccccgacac ccgccaacac ccgctgacgc   2040
gccctgacgg gcttgtctgc tcccggcatc cgcttacaga caagctgtga ccgtctccgg   2100
gagctgcatg tgtcagaggt tttcaccgtc atcaccgaaa cgcgcgaggc agctgcggta   2160
aagctcatca gcgtggtcgt gaagcgattc acagatgtct gcctgttcat ccgcgtccag   2220
ctcgttgagt ttctccagaa gcgttaatgt ctggcttctg ataaagcggg ccatgttaag   2280
ggcggttttt tcctgtttgg tcactgatgc ctccgtgtaa gggggatttc tgttcatggg   2340
ggtaatgata ccgatgaaac gagagaggat gctcacgata cgggttactg atgatgaaca   2400
tgcccggtta ctggaacgtt gtgagggtaa acaactggcg gtatggatgc ggcgggacca   2460
gagaaaaatc actcagggtc aatgccagcg ctcatgagcc cgaagtggcg agcccgatct   2520
tccccatcgg tgatgtcggc gatataggcg ccagcaaccg cacctgtggc gccggtgatg   2580
ccggccacga tgcgtccggc gtagaggatc gagatccatt tacgttgaca ccatcgaatg   2640
gtgcaaaacc tttcgcggta tggcatgata gcgcccggaa gagagtcaat tcagggtggt   2700
gaatgtgaaa ccagtaacgt tatacgatgt cgcagagtat gccggtgtct cttatcagac   2760
cgtttcccgc gtggtgaacc aggccagcca cgtttctgcg aaaacgcggg aaaaagtgga   2820
agcggcgatg gcggagctga attacattcc caaccgcgtg gcacaacaac tggcgggcaa   2880
acagtcgttg ctgattggcg ttgccacctc cagtctggcc ctgcacgcgc cgtcgcaaat   2940
tgtcgcggcg attaaatctc gcgccgatca actgggtgcc agcgtggtgg tgtcgatggt   3000
agaacgaagc ggcgtcgaag cctgtaaagc ggcggtgcac aatcttctcg cgcaacgcgt   3060
cagtgggctg atcattaact atccgctgga tgaccaggat gccattgctg tggaagctgc   3120
ctgcactaat gttccggcgt tatttcttga tgtctctgac cagacaccca tcaacagtat   3180
tattttctcc catgaagacg gtacgcgact gggcgtggag catctggtcg cattgggtca   3240
ccagcaaatc gcgctgttag cgggcccatt aagttctgtc tcggcgcgtc tgcgtctggc   3300
tggctggcat aaatatctca ctcgcaatca aattcagccg atagcggaac gggaaggcga   3360
ctggagtgcc atgtccggtt ttcaacaaac catgcaaatg ctgaatgagg gcatcgttcc   3420
cactgcgatg ctggttgcca acgatcagat ggcgctgggc gcaatgcgcg ccattaccga   3480
gtccgggctg cgcgttggtg cggatatctc ggtagtggga tacgacgata ccgaagacag   3540
ctcatgttat atcccgccgt taaccaccat caaacaggat tttcgcctgc tggggcaaac   3600
cagcgtggac cgcttgctgc aactctctca gggccaggcg gtgaagggca atcagctgtt   3660
gcccgtctca ctggtgaaaa gaaaaaccac cctggctcga gaaatcataa aaaatttatt   3720
tgctttgtga gcggataaca attataatag attcaattgt gagcggataa caatttcaca   3780
catctagaaa taattttatt taactttaag aaggagatat acatatgcac aaatgcgata   3840
tcaccctgca ggaaatcatc aaagacctga attctctgac cgaacagaaa accctgtgca   3900
ccgaactgac cgttaccgac atcttcgctg cttcgaaatg caccaccgaa aaagaaacct   3960
tctgccgtgc tgctaccgtt ctgcgtcagt tctactctca ccacgaaaaa gacacccgtt   4020
gcctgggtgc taccgctcag cagttccacc gtcacaaaca gctgatccgt ttcctgaaac   4080
gtctggaccg taacctgtgg ggtctggctg gtctgaacag ctgcccggtt aaagaagcta   4140
accagtctac cctggaaaac ttcctggaac gtctgaaaac catcatggac gaaaaagact   4200
ctaaatgctc ttcttaataa ggatccggct gctaacaaag cccgaaagga agctgag      4257
```